(12) United States Patent
Vogl et al.

(10) Patent No.: US 11,850,778 B2
(45) Date of Patent: Dec. 26, 2023

(54) METHOD FOR PRODUCING A SYRINGE WITH AN INTEGRATED CLOSURE ELEMENT

(71) Applicant: Gerresheimer Regensburg GmbH, Regensburg (DE)

(72) Inventors: Maximilian Vogl, Mantel (DE); Ulf Kirschner, Wernberg-Köblitz (DE); Jessica Kreher, Schwandorf (GE)

(73) Assignee: Gerresheimer Regensburg GmbH, Regensburg (DE)

( * ) Notice: Subject to any disclaimer, the term of this patent is extended or adjusted under 35 U.S.C. 154(b) by 1248 days.

(21) Appl. No.: 16/374,999

(22) PCT Filed: Sep. 29, 2017

(86) PCT No.: PCT/EP2017/074788
§ 371 (c)(1),
(2) Date: Apr. 4, 2019

(87) PCT Pub. No.: WO2018/065312
PCT Pub. Date: Apr. 12, 2018

(65) Prior Publication Data
US 2019/0299507 A1    Oct. 3, 2019

(30) Foreign Application Priority Data

Oct. 4, 2016  (DE) .................. 10 2016 118 767.4
Oct. 4, 2016  (DE) .................. 10 2016 118 768.2

(51) Int. Cl.
*B29L 31/00*       (2006.01)
*B29C 45/16*       (2006.01)
(Continued)

(52) U.S. Cl.
CPC .......... *B29C 45/261* (2013.01); *A61M 5/347* (2013.01); *B29C 45/16* (2013.01);
(Continued)

(58) Field of Classification Search
None
See application file for complete search history.

(56) References Cited

U.S. PATENT DOCUMENTS 3,402,713 A * 9/1968 Senkowski ........... A61M 5/347
                                              264/318
5,975,381 A * 11/1999 Revenu ................ B65D 47/128
                                              220/792
(Continued)

FOREIGN PATENT DOCUMENTS

DE     69333607 T2    9/2005
EP     0073356 A1    3/1983
(Continued)

OTHER PUBLICATIONS

DE69333607 T2—English machine translation of Abstract.
(Continued)

*Primary Examiner* — Armand Melendez
(74) *Attorney, Agent, or Firm* — Leydig Voit & Mayer, Ltd.

(57) ABSTRACT

The invention relates to a method for producing a syringe with an integrated closure element, which method comprises the following method steps:
a) making available an injection moulding tool which comprises a first, a second and a third tool portion, wherein the first tool portion has a mould cavity open at both sides and extending along an axial direction (X), and wherein the second tool portion has a first injection moulding core and the third tool portion has a second injection moulding core;
b) closing the injection moulding tool such that the first tool portion contacts the second and third tool portion, and the first and second injection moulding core each enter the mould cavity of the first tool portion through (Continued)

an opening and finally contact each other, as a result of which these tool portions form a first structural cavity;
c) injecting a first plastic material into the first structural cavity, as a result of which a hollow cylindrical syringe body is formed with an end region at its distal end, wherein the end region has an attachment element, provided with an inner thread, and a hollow cylindrical endpiece which is at least partially bounded by the attachment element;
d) cooling the tool portions, as a result of which the syringe body cools and hardens;
e) bringing the first tool portion into contact with a fourth tool portion provided with a mould cavity closed at one end, as a result of which a second structural cavity is formed at the distal end of the syringe body;
f) injecting a second plastic material into the second structural cavity, as a result of which the closure element is integrally formed on the attachment element, wherein the first and the second plastic material do not enter into a cohesive connection.

19 Claims, 17 Drawing Sheets

(51) Int. Cl.
| | | |
|---|---|---|
| *B29C 45/26* | (2006.01) | |
| *A61M 5/34* | (2006.01) | |
| *B29C 45/33* | (2006.01) | |
| *B29C 45/44* | (2006.01) | |
| *A61M 5/50* | (2006.01) | |
| *A61M 5/31* | (2006.01) | |
| *B29K 23/00* | (2006.01) | |
| *B29L 31/56* | (2006.01) | |
| *B29C 45/36* | (2006.01) | |

(52) U.S. Cl.
CPC .......... *B29C 45/1675* (2013.01); *B29C 45/33* (2013.01); *B29C 45/44* (2013.01); *A61M 5/5086* (2013.01); *A61M 2005/312* (2013.01); *A61M 2005/3104* (2013.01); *B29C 45/2618* (2013.01); *B29C 45/36* (2013.01); *B29C 2045/1601* (2013.01); *B29K 2023/04* (2013.01); *B29K 2023/10* (2013.01); *B29K 2023/38* (2013.01); *B29L 2031/56* (2013.01); *B29L 2031/7544* (2013.01)

(56) References Cited

U.S. PATENT DOCUMENTS

| | | | | |
|---|---|---|---|---|
| 6,120,714 | A * | 9/2000 | Allan | B29C 45/16 |
| | | | | 264/328.8 |
| 6,706,231 | B1 * | 3/2004 | Ingram | B29C 43/42 |
| | | | | 264/297.6 |
| 2004/0169318 | A1 * | 9/2004 | Chiba | B29C 45/572 |
| | | | | 264/328.12 |
| 2006/0178627 | A1 * | 8/2006 | Geiger | A61M 5/3134 |
| | | | | 215/250 |
| 2008/0102235 | A1 | 5/2008 | Skigen et al. | |
| 2011/0052849 | A1 * | 3/2011 | Skigen | B29C 45/1675 |
| | | | | 264/255 |
| 2011/0254202 | A1 * | 10/2011 | Aeschlimann | A61M 5/158 |
| | | | | 425/577 |
| 2016/0199591 | A1 * | 7/2016 | Matsui | B29C 45/261 |
| | | | | 425/129.1 |
| 2016/0250420 | A1 * | 9/2016 | Maritan | A61M 5/3202 |
| | | | | 604/192 |

FOREIGN PATENT DOCUMENTS

| | | |
|---|---|---|
| EP | 0849173 A1 | 6/1998 |
| EP | 1024091 A1 | 8/2000 |
| EP | 1600190 A1 | 11/2005 |
| JP | 2003311780 A | 11/2003 |
| JP | 2004329504 A | 11/2004 |

OTHER PUBLICATIONS

EP0073356 A1—English machine translation of Abstract.
EP0849173 A1—English machine translation of Abstract.
EP1024091 A1—English machine translation of Abstract.
EP1600190 A1—English machine translation of Abstract.
JP2003311780 A—English machine translation of Abstract.
JP2004329504 A—English machine translation of Abstract.
International Search Report dated Jan. 10, 2018 for PCT/EP2017/074788.
Anonymous: II Entwicklungsprojekt TELC in Zusammenarbeit zwischen den Firmen Gerresheimer Bunde GmbH und der Braunform GmbH, reinaum online, Mar. 10, 2013 (Mar. 10, 2013), p. 46 . Retrieved from the Internet: URL:http://www.braunform.com/de/downloads/Veroeffentlichungen/altere/2013 Reinraum-printline TELC.pdf—original.
Anonymous: TELC development project in cooperation between Gerresheimer Bünde GmbH and Braunform GmbH, Mar. 10, 2013 (Mar. 10, 2013), p. 46—English translation.

* cited by examiner

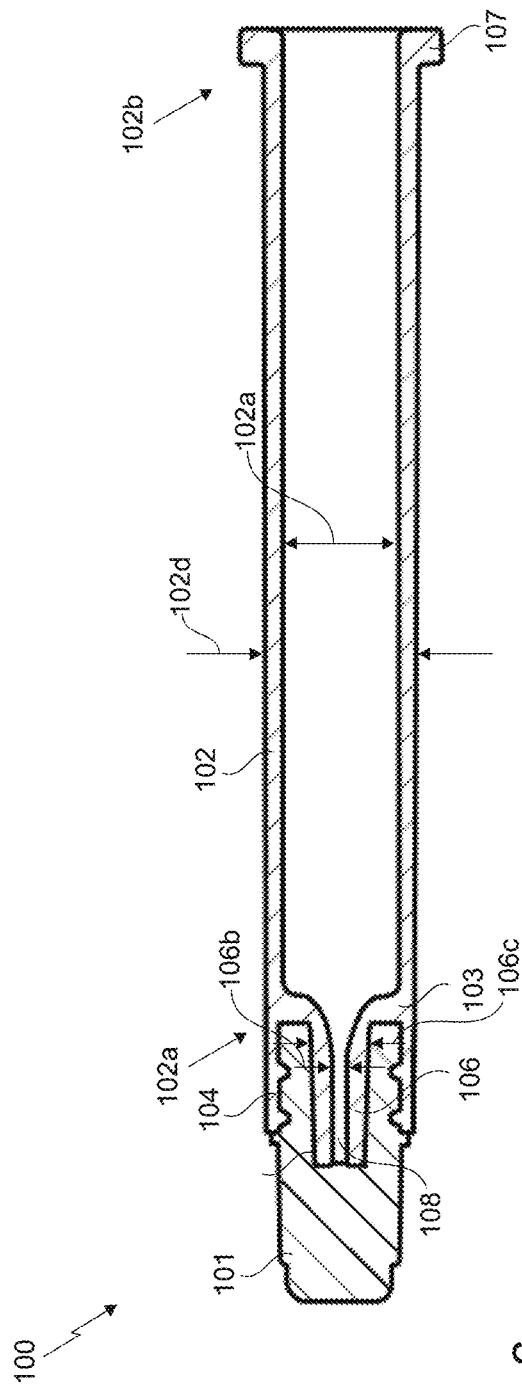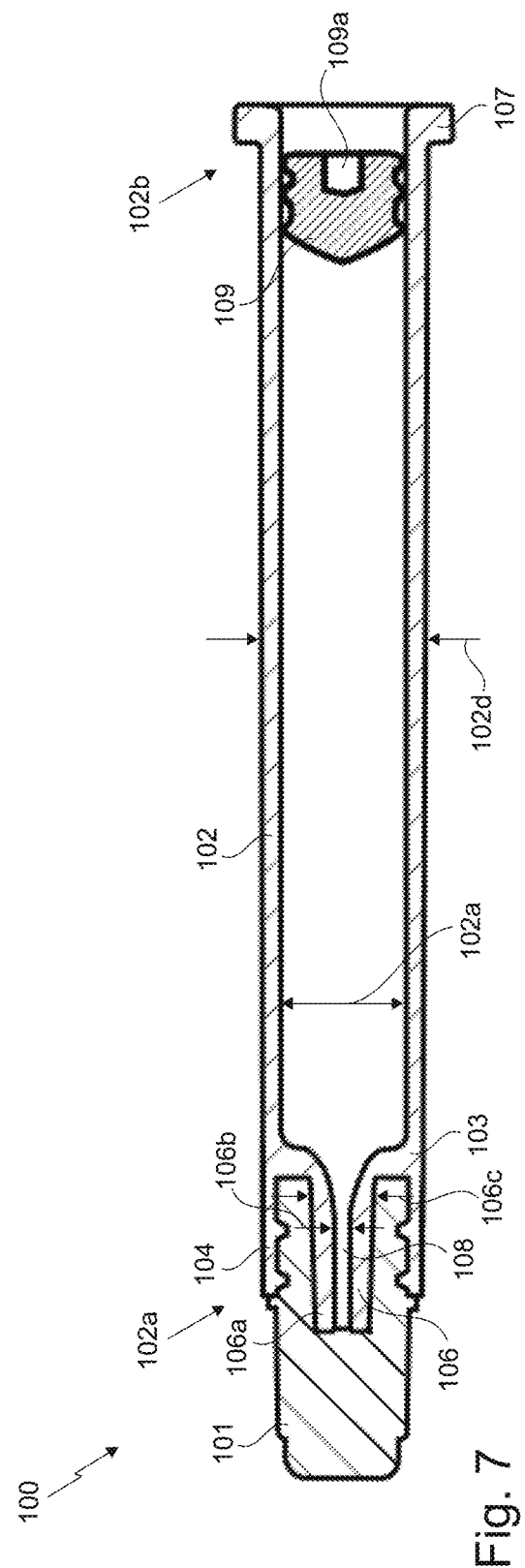

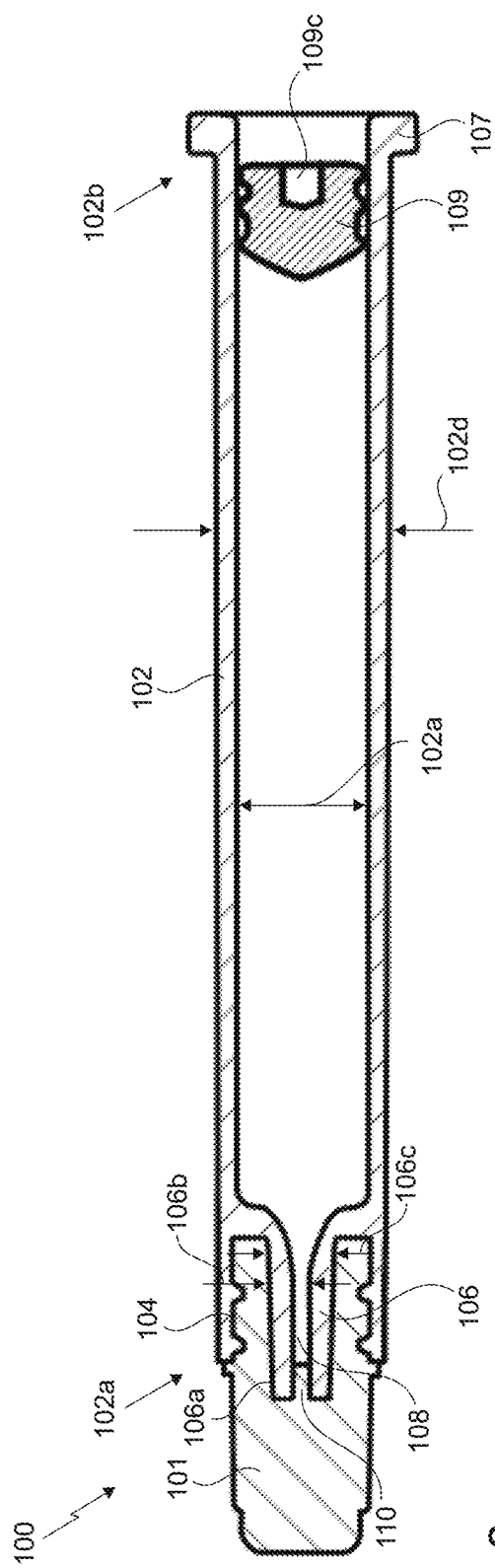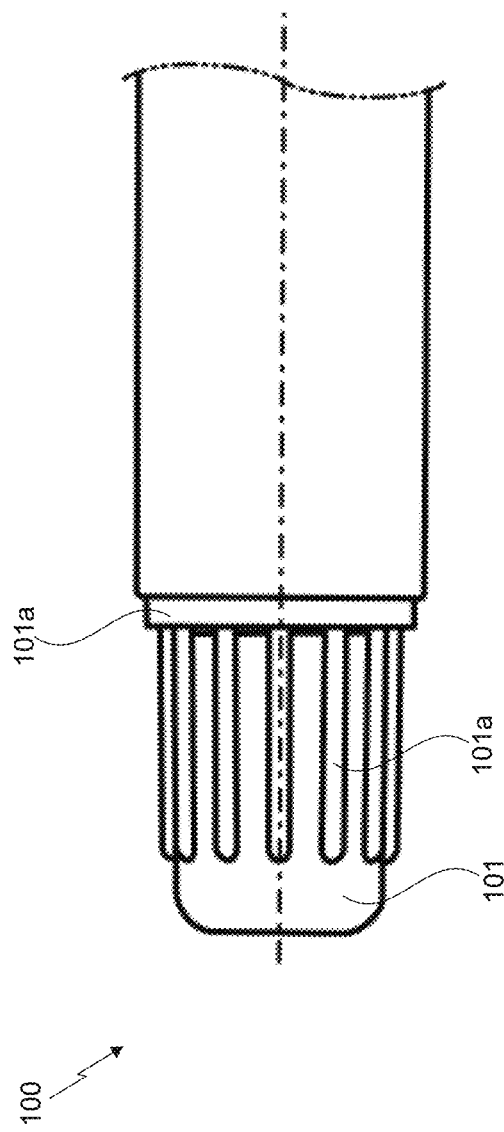
Fig. 8
Fig. 9

METHOD FOR PRODUCING A SYRINGE WITH AN INTEGRATED CLOSURE ELEMENT

This application is the national stage of International Patent Application No. PCT/EP2017/074788 filed on Sep. 29, 2017, which in turn claims priority from German Patent Application No. 10 2016 118 768.2 filed on Oct. 4, 2016, and German Patent Application No. 10 2016 118 767.4 filed on Oct. 4, 2016, the disclosures of which are incorporated herein by reference in their entirety.

TECHNICAL FIELD

The present invention relates to an injection moulding process for producing a syringe with an integrated closure element, and to a syringe with an integrated closure element.

BACKGROUND

The use of so-called prefilled plastic syringes is now widespread in medicine. These syringes are delivered to the user already containing the medium to be used and have the advantage that their handling is very simple because the medium does not have to be transferred into the syringe prior to use. Furthermore, the likelihood of using the wrong drug is very low, even in an emergency. Such syringes are also used in the pharmaceutical and biotech industries. For vaccines and many other drugs they are now the packaging of choice.

Typically, such syringes have an end piece designed as a cone with an outer diameter that tapers continuously. Such cones are predominantly designed as a male luer cone. A luer fitting, lock or slip system is a standardised (ISO 594) connection system for tube systems in the medical field and ensures compatibility between different manufacturers. It is used inter alia in syringes, cannulas and infusion tubes. A male luer cone is a flat (6% pitch), hollow cone with a relatively large surface area and thus good adhesion with a plugged (female) luer fitting, such as a cannula. The conical design of the two connecting parts achieves a sufficient seal.

It is often necessary to secure the connection of a syringe to a transfer system, such as a tube or the like, against undesired loosening. For this purpose, the syringes are equipped with an attachment element that has an inner thread and is thus also frequently referred to as a union nut. By means of the inner thread, the syringe can be reversibly connected to corresponding transfer systems, thus preventing an unwanted detachment of the connection. To ensure compatibility with a maximum number of attachment elements, the attachment element or the inner thread have a standardised design. The luer lock system is such a standardised bolt system. The luer lock connection has been adopted worldwide for reversible connections of syringes, cannulas, infusion tubes, spinal needles, etc.

The prefilled syringes can be fitted retrospectively with attachable luer lock connectors. However, there are also syringe bodies that are already made with a luer lock connector. Such pre-fillable syringes (syringe bodies) are produced by the primary packaging manufacturer under clean room conditions, packaged, sterilised and delivered ready for filling directly to the clean room of the filler, for example a pharmacist. They can then be used for filling without further treatment steps. Usually, the inner walls of the syringes are also siliconised so the plunger stopper moves easily in the syringe and still provides a sufficient seal between the syringe body and the piston. The prefillable syringes are filled by the filler from the proximal side or the flange side. Consequently, the distal end of the syringe must be closed beforehand. Usually this is a resilient, sealing closure that is removed before the use of the syringe. This closure can be made of either a rubber or a resilient thermoplastic. In the prior art known thus far, such a closure is mounted on the syringe during production. A disadvantage of such a subsequently integrated mounting of a closure is increased expenditure for automation. On the one hand, this involves further costs due to the additionally required sophisticated equipment, such as robotic arms. The cycle times for manufacture of a single syringe are also extended. In addition, there is an increased risk of contamination of the head region of the syringe since it is open at the start of processing and is only subsequently closed.

The object of the present invention is to provide a method for producing a prefillable plastic syringe that solves the aforementioned problems and thus ensures a simple and cost-effective production of such a syringe.

SUMMARY

The object is achieved by a method according to claim 1. Accordingly, an injection moulding process is provided for producing a syringe with an integrated closure element, which process comprises the following steps:
  a) providing an injection moulding tool which comprises a first, a second and a third tool portion, wherein the first tool portion has a mould cavity open at both sides and extending along an axial direction (X), and wherein the second tool portion has a first injection moulding core and the third tool portion has a second injection moulding core;
  b) closing the injection moulding tool such that the first tool portion contacts the second and third tool portion, and the first and second injection moulding cores each enter the mould cavity of the first tool portion through an opening and finally contact each other, as a result of which these tool portions form a first cavity;
  c) injecting a first plastic material into the first cavity, as a result of which a hollow cylindrical syringe body is formed with an end region at its distal end, wherein the end region has an attachment element provided with an inner thread, and a hollow cylindrical end piece which is at least partially bordered by the attachment element;
  d) cooling the tool portions, as a result of which the syringe body cools and hardens;
  e) bringing the first tool portion into contact with a fourth tool portion provided with a mould cavity closed at one end, as a result of which a second cavity is formed at the distal end of the syringe body;
  f) injecting a second plastic material into the second cavity, as a result of which the closure element is integrally formed on the attachment element, wherein the first and the second plastic material do not enter into a cohesive connection.

Using the production method according to the invention, a syringe is provided with an attachment element that is preferably configured as a luer lock system. The syringe is provided with an integrated closure element that is moulded by the method according to the invention directly onto the attachment element. Because the two plastic materials of the attachment element and closure element do not enter into a cohesive connection, the closure element is detachable from the attachment element. In step b), an attachment element provided with an inner thread is formed on which in step f) the closure element is integrally formed. Consequently, the closure element is provided with an outer thread since the inner thread acts as a shaping structure. This outer thread thus engages the inner thread of the attachment element. Because the two plastic materials of the attachment element and closure element do not enter into a cohesive connection, the attachment element and closure element are connected in a form-locking or force-locking manner by means of a screw connection. The user can therefore loosen the closure element by a rotational movement of the attachment element. According to a preferred embodiment, the fourth tool portion is heated in step e).

The cooling of the tool portions and the cooling and hardening of the syringe body are necessary to ensure that the first and second plastic materials do not enter into a cohesive connection. The syringe body should in this case be cooled to a temperature low enough that the injection of the second plastic material causes no melting of the contacted surfaces of the syringe body.

The method according to the invention is much simpler and more effective than the methods known from the prior art, since a subsequent mounting of a closure is omitted. Furthermore, it is no longer necessary to produce the closure part in a separate manufacturing step, as a result of which the production costs and use of materials are reduced. The syringe according to the invention is thus more economical and easier to produce because additional costs for manufacture and assembly of a closure part are eliminated. Furthermore, the risk of contamination of the head region of the syringe before the syringe is closed is eliminated because it is possible to produce the closure element in the same production step as the syringe body.

According to at least one embodiment, the end region has an attachment element provided with an inner thread and at least one recess.

According to at least one embodiment, the closure element is integrally formed on the attachment element by injecting the second plastic material into the second cavity, as a result of which a protrusion is formed in the at least one recess.

Preferably, the first and second injection moulding cores extend along the axial direction (X). Preferably, the first injection moulding core has a first cylindrical portion having a first diameter and a second cylindrical portion having a second, smaller diameter. Preferably, the first and the second cylindrical portion are adjacent in the axial direction (X). According to a preferred embodiment, the second injection moulding core has a mould cavity open on one side in the axial direction (X). Advantageously, the second injection moulding core also has a recess in an inner wall bordering the mould cavity in the axial direction (X).

According to a preferred embodiment, in process step b), an inner wall of the mould cavity of the first tool portion and an outer wall of the first cylindrical portion of the first injection moulding core form a first portion of the first cavity, by means of which the hollow cylindrical syringe body is formed. Preferably, the injection moulding core is introduced centrally into the mould cavity such that a distance between the inner wall of the mould cavity of the first tool portion and the outer wall of the first cylindrical portion is constantly equal in each radial direction. Thus, a constant wall thickness of the syringe cylinder is ensured.

Preferably, when the two injection moulding cores come into contact in process step b), the second cylindrical portion of the first injection moulding core is received in part in the recess of the second injection moulding core. Advantageously, a third cavity is formed by the mould cavity of the second injection moulding core and the second cylindrical portion of the first injection moulding core, by means of which the preferably conically shaped end piece is formed. Preferably, an outer wall of the second cylindrical portion and an inner wall of the mould cavity of the second injection moulding core border this third cavity.

The second cylindrical portion thus forms the channel of the end piece. It is advantageous that the second cylindrical portion is received in the recess of the inner wall axially bordering the mould cavity. The second cylindrical portion thus projects over this inner wall that forms the distal end of the end piece. This configuration ensures that no first plastic material enters the channel of the end piece and thus closes it. Here too it is advantageous if the second cylindrical portion is introduced centrally into the mould cavity of the second injection moulding core in order to ensure a constant wall thickness of the end piece. Preferably, the mould cavity of the second injection core is configured conically so that a conical end piece can be formed.

According to at least one embodiment, the method proposed here also comprises a second alternative:
 a) providing an injection moulding tool which comprises a first, a second and a third tool portion, wherein the first tool portion has a mould cavity open at both sides and extending along a first axial direction, and wherein the second tool portion has a first injection moulding core and the third tool portion has a second injection moulding core;
 b) closing the injection moulding tool such that the first tool portion contacts the second and third tool portion, and the first and second injection moulding core each enter the mould cavity of the first tool portion through an opening and finally contact each other, as a result of which these tool portions form a first cavity;
 c) injecting a first plastic material into the first cavity, as a result of which a hollow cylindrical syringe body is formed with an end region at its distal end, wherein the end region has an attachment element, provided with an inner thread and at least one recess, and a hollow cylindrical end piece which is at least partially bordered by the attachment element;
 d) cooling the tool portions, as a result of which the syringe body cools and hardens;
 e) bringing the first tool portion into contact with a fourth tool portion provided with a mould cavity closed on one side, as a result of which a second cavity is formed at the distal end of the syringe body;
 f) injecting a second plastic material into the second cavity, as a result of which the closure element is integrally formed on the attachment element, as a result of which a protrusion is formed in the at least one recess, wherein the first and the second plastic material do not enter into a cohesive connection.

Through the production method proposed in the above alternative, a syringe having an attachment element is provided that is preferably designed as a luer lock system. The syringe is provided with an integrated closure element, which is moulded by the method according to the invention directly onto the attachment element. Because the two plastic materials of the attachment element and closure element do not enter into a cohesive connection, the closure element is detachable from the attachment element. In step b), an attachment element is formed provided with an inner thread and at least one recess, on which attachment element the closure element is integrally formed in step f). Consequently, the closure element is provided with an outer thread and with at least one protrusion because the inner thread and the recess act as shaping structures. This outer thread accordingly engages the inner thread of the attachment element, and the at least one protrusion engages the recess of the attachment element. This protrusion represents what is known as a tamper evidence feature. Under a tamper evidence feature in this connection are subsumed all the elements that are able to show whether an item, especially a syringe, has already been used, such that based on the quality of these elements the originality condition of a product is obviously visible. In this case, the first and the second plastic materials are in a liquid state.

Because the two plastic materials of the attachment element and closure element do not enter into a cohesive connection, the attachment element and closure element are connected in a form-locking and force-locking manner by means of a screw connection. The user can thus loosen the closure element from the attachment element by a rotational movement of the closure element. By rotating the closure element, the protrusions arranged thereon are irreversibly deformed upon exiting the recesses such that the closure element shows whether the syringe has already been used.

The cooling and hardening of the syringe body in process step d) ensures that the first and the second plastic materials do not enter into a cohesive connection. The syringe body should in this case be cooled to a temperature low enough that the injection of the second plastic material causes no melting of the contacted surfaces of the syringe body.

The method according to the invention is much simpler and more effective than the methods known from the prior art, since a subsequent mounting of a closure is omitted. Furthermore, it is no longer necessary to produce the closure part in a separate manufacturing step, thereby reducing production costs and use of materials. The syringe according to the invention is thus more economical and easier to produce because additional costs for manufacture and assembly of a closure part are eliminated. Furthermore, the risk of contamination of the head region of the syringe before the syringe is closed is eliminated since it is possible to produce the closure element in the same procedure as the syringe body. In addition, the formation of the at least one protrusion creates a tamper evidence feature directly on the product, which yields greater safety in terms of misuse or mistaken re-use since it can be seen directly on the product itself whether the product has already been used. In addition, the protrusions formed eliminate the necessity of packaging with additional tamper evidence features.

Preferably, the at least one recess is surrounded by an outer and an inner wall portion, the outer wall portion forming a part of the outer surface of the attachment element. The recess is thus situated in a radial direction between two wall portions. The at least one recess is configured in the circumferential direction such as to enable the closure element to be unscrewed and at the same time to ensure a deformation of the at least one protrusion.

Preferably, the pitch of the inner thread of the attachment element corresponds to the inclination of the at least one protrusion. This is necessary to permit unscrewing of the closure element without the closure element tilting due to the at least one protrusion in the attachment element.

According to a further embodiment, the attachment element provided with an inner thread is formed by a fourth cavity, which is formed by an outer region of the second injection moulding core and the inner wall of the mould cavity of the first tool portion. Preferably, the outer region of the second injection moulding core has recesses and/or protrusions by which the inner thread is formed on the attachment element.

Preferably, the second cavity formed in process step e) is formed by an inner wall of the mould cavity of the fourth tool portion and by outer regions of the end region of the syringe body. These outer regions are preferably the outer wall of the end piece and the inner wall or rather the inner thread of the attachment element. According to a preferred embodiment, recesses and/or protrusions are arranged on the inner wall of the mould cavity of the fourth tool portion such that the closure element is formed with corresponding protrusions, for example longitudinal ribs. Such protrusions improve the feel of the closure element or rather these protrusions form a grip for twisting off the closure element.

Advantageously, the second injection moulding core is demoulded from the attachment element of the syringe body between process steps d) and e). Preferably, the second injection moulding core is demoulded from the inner thread of the attachment element by a rotational movement. Advantageously, the rotational movement of the second injection moulding core is driven by an electric motor, a hydraulic drive or another drive.

Preferably, the third tool portion is removed from the first tool portion between process steps d) and e). This can take place, for example, by a movement of the first and third tool portions relative to one another. Such a relative movement could be a rotational movement or a translational movement. Preferably, in process step e) the first and the fourth tool portions are also moved relative to one another such that these contact or abut each other. This movement can also be a rotational movement or a translational movement.

According to a further preferred embodiment, the first plastic material is injected through a first injection nozzle that is arranged in the second tool portion. However, it would also be conceivable to arrange the first injection nozzle in the first tool portion. It is also advantageous if the second plastic material is injected through a second injection nozzle arranged in the fourth tool portion.

Preferably, the mould cavity of the first tool portion has a first opening that the first injection moulding core enters in step b). Advantageously, this first opening is arranged in the region of the first cavity, which forms the proximal end of the syringe body. Preferably, the mould cavity of the first tool portion has a second opening that the second injection moulding core enters in process step b).

According to a preferred embodiment, the second tool portion has a recess that is open towards the first cavity and by means of which a finger rest is formed on the proximal end of the syringe body. Preferably, the first injection nozzle is connected to this recess.

Preferably, the second tool portion having the first injection moulding core is designed to be T-shaped at least in part. Preferably, both the first and the second tool portions have end faces that extend along a second direction (Y) that runs perpendicular to the axial direction. Preferably, after process step b), these end faces firmly abut one another. Preferably, the first cavity or rather the first opening of the mould cavity of the first tool portion are closed in the axial direction by the second tool portion.

Preferably, the third tool portion having the second injection moulding core is designed to be T-shaped at least in part. Preferably, both the first and the third tool portions have end faces that extend along a second direction (Y) that runs perpendicular to the axial direction. Preferably, after process step b), these end faces firmly abut one another. Preferably, the first cavity or rather the second opening of the mould cavity of the first tool portion are closed in the axial direction by the third tool portion.

According to another preferred embodiment, the first, second, third and fourth tool portions are individually heated and cooled. The heating is preferably carried out by a laser. The laser wavelength is advantageously tuned such that the greatest possible proportion of the laser energy can be absorbed by the tool material. The use of a laser has the advantage that selection of the tool portion to be heated can be done very precisely. However, other heating methods would also be conceivable, such as heating wires or the like.

Advantageously, the cooling of the tool portions is carried out by means of a coolant. Preferably, such coolants contain water and/or nitrogen and/or $CO_2$.

The cooling of the first, second and third tool portions or rather of the syringe body in process step d), and the associated thermal contraction of the material, cause a volume shrinkage of the syringe body. Accordingly, this advantageously already demoulds from the mould cavity of the first tool portion. However, the syringe body advantageously remains arranged on the first injection moulding core and can therefore undergo the further process steps.

According to another preferred embodiment, after process step f), the fourth tool portion is cooled, as a result of which the closure element is cooled and demoulded from the mould cavity of the fourth tool portion through the associated volume shrinkage. Preferably, the syringe body with the integrated closure element is then ejected and is supplied to further process steps.

According to a further idea of the invention, the first moulding core is designed telescopically. Preferably, the second cylindrical portion is displaceable relative to the first portion. According to a preferred embodiment, the first cylindrical portion has a through-hole in which a further cylindrical element that includes the second cylindrical portion is movably arranged. This further cylindrical element advantageously can be shifted back and forth in the axial direction (X) by means of a drive. Preferably, the second cylindrical portion in process steps b) to d) is in a maximum axial position such that the second cylindrical portion contacts the second injection moulding core. Advantageously, between process steps d) and e) the second portion is shifted in the axial direction away from the third tool portion. Preferably, in the subsequent process step f), the second plastic material then enters the channel of the end piece, as a result of which a seal is created on the channel piece Because the first and second plastic materials do not enter into a cohesive connection, the seal is detachable. Preferably, the seal with the closure element is removed from the syringe before the syringe is used.

Preferably, the first and the second plastic material are different materials. According to a particularly preferred embodiment, the first plastic material is a polymer plastic material, preferably a polyolefin, for example polypropylene or polyethylene, particularly preferably a cyclic olefin polymer (COP) or a cyclic olefin copolymer (COC). COC and COP, in contrast to the semi-crystalline polyolefins like polyethylene and polypropylene, are amorphous and therefore transparent. Such plastic materials are characterised by excellent biocompatibility, in particular blood compatibility, and extremely low water absorption/water vapour permeability. In addition, these plastic materials show no reaction with the commonly used medicines.

According to a further preferred embodiment, the second plastic material is a thermoplastic elastomer.

According to a further preferred embodiment, the first and the second plastic materials are the same materials. Advantageously, this material is a polymer plastic material, preferably a polyolefin, for example polypropylene or polyethylene, particularly preferably a cyclic olefin polymer (COP) or a cyclic olefin copolymer (COC). As already mentioned, COC/COP are particularly suitable for prefillable syringes due to their high barrier properties. Such a design is particularly advantageous for prefillable syringes, since, during the entire storage time of the prefilled syringe, the closure material is in contact with the medium (drug/vaccine) in the syringe. The abovementioned properties of COP and COC ensure the least possible influence of the closure material on the medium.

The plastic material to be injected is preferably plasticised in a plasticising unit. Such a plasticising unit comprises inter alia a plasticising cylinder having a screw and heating elements. The plasticised plastic material is then preferably supplied via a runner of the corresponding injection nozzle.

In the injection phase, the plasticised plastic material is injected through the respective injection nozzle under high pressure into the cavity. The pressure is preferably between a value of about 1 MPa and about 200 MPa. During the injection, the plasticised plastic material preferably has a temperature of some 100° C. However, the cavity-forming elements have a lower temperature. Upon contact with the comparatively cold wall regions of the cavity, the plastic material solidifies upon reaching the solidification point of the respective material. To ensure the most homogeneous possible distribution of the plastic material in the cavity, the plastic material must be introduced quickly into the cavity. The injection rate is preferably some 10 ccm/s. COC and COP have a comparatively low viscosity and are particularly well-suited for the error-free production of finely textured, thin-walled components even over long flow paths.

According to an advantageous idea of the invention, the plastic materials are fed in each case via a hot runner of the corresponding injection nozzle. As a result, the sprue system leading from the plasticising unit to the respective injection nozzle is advantageously thermally insulated from the injection moulding tool. With a different sprue system, after the cavity is filled, the remaining plastic material solidifies in the sprue system. This so-called sprue must then be separated from the moulded part. This requires additional tools. Furthermore, the additional plastic material must be disposed of. When using a hot runner, the sprue system is maintained at a correspondingly high temperature so that the sprue does not solidify.

In a preferred embodiment, two, more preferably three, and particularly preferably more than three recesses are formed on the attachment element, and protrusions complementary thereto are formed on the closure element. In an arrangement of two or more recesses or protrusions, these are preferably offset in a circumferential direction at equal angular intervals to each other. Thus, for example, two protrusions or recesses would be offset to each other by 180°, three protrusions or recesses by 120°, and four protrusions or recesses by 90°.

In a particularly preferred embodiment, after process step d), in a further process step d2), a sealing element is attached to the fourth tool portion, the fourth tool portion having a holding element projecting into the mould cavity of the fourth tool portion that is designed to hold the sealing element. In addition, the sealing element is preferably pressed in process step e) against the hollow cylindrical end piece of the syringe body. The hollow cylindrical end piece is sealed by pressing the sealing element against the hollow cylindrical end piece of the syringe body. Preferably, the sealing element is made of a rubber material. However, the sealing element can be made of any other material, such as plastic material, that causes no reaction with the conventionally used drugs or substances. The arrangement of a sealing element creates no direct contact of the second plastic material with the drug, which is why the selection of the second plastic material is not limited by the drug compatibility.

Preferably, after completion of process step f), the sealing element is enclosed by the second plastic material such that the sealing element, after the demoulding of the fourth tool portion, is still pressed against the hollow cylindrical end piece of the syringe body. This is advantageous in order to prevent slipping of the sealing element after manufacture and to ensure a reliable seal of the syringe. Accordingly, at least in the circumferential direction, the sealing element is surrounded completely, and in a first axial direction X at least in part, by the second plastic material.

Particularly preferably, between process steps d) and e), the second injection moulding core is demoulded from the attachment element of the syringe body and the third tool portion is removed from the first tool portion, the second injection moulding core being demoulded by a rotational movement of the second injection moulding core from the inner thread and the at least one recess of the attachment element. A rotational movement to remove the second injection moulding core is advantageous to avoid damaging the formed inner thread and the at least one recess. Here, the second injection moulding core is rotatably mounted in the fourth tool portion.

Furthermore, after completion of the method, all the tool halves are demoulded from each other by a movement relative to one another and/or to the syringe body. This movement can be both a rotational and a translational movement.

Preferably, the first and the second plastic materials are different materials. According to a particularly preferred embodiment, the first plastic material is a polymer plastic material, preferably a polyolefin, for example polypropylene or polyethylene, particularly preferably a cyclic olefin polymer (COP) or a cyclic olefin copolymer (COC). COC and COP, in contrast to the semi-crystalline polyolefins like polyethylene and polypropylene, are amorphous and therefore transparent. Such plastic materials are characterised by excellent biocompatibility, in particular blood compatibility, and extremely low water absorption/water vapour permeability. In addition, these plastic materials show no reaction with commonly used medicines. This embodiment is particularly advantageous if an additional sealing element is provided in the closure element, since in this way, the second plastic material does not come into contact with the drug and therefore only the sealing element must meet the special requirements.

According to a further preferred embodiment, the second plastic material is a thermoplastic elastomer.

According to a further preferred embodiment, the first and the second plastic materials are the same materials. Advantageously, this material is a polymer plastic material, preferably a polyolefin, for example polypropylene or polyethylene, particularly preferably a cyclic olefin polymer (COP) or a cyclic olefin copolymer (COC). As already mentioned, COC/COP are particularly suitable for prefillable syringes due to their high barrier properties. Such a design is particularly advantageous for prefillable syringes, since during the entire storage time of the prefilled syringe the closure material is in contact with the medium (drug/vaccine) in the syringe. The abovementioned properties of the COP and COC ensure the least possible influence of the closure material on the medium. This embodiment is particularly relevant without the use of an additional sealing element, because there, the second plastic material is in direct contact with the drug.

The object of the invention is also achieved by a syringe having an integrally formed closure element and at least one protrusion arranged on the closure element, which protrusion is produced by a process according to one of the preceding embodiments.

In a preferred embodiment of the syringe, a sealing element is arranged on the closure element.

Further advantages, aims and features of the present invention are explained with reference to the following description of the accompanying drawings. Similar components may have the same reference numerals in the various embodiments.

BRIEF DESCRIPTION OF THE DRAWINGS

FIG. 6 is a sectional view of a syringe body;
FIG. 7 is a sectional view of a syringe body according to another embodiment;
FIG. 8 is a sectional view of a syringe body according to another embodiment;
FIG. 9 is a side view of the closure element.

DETAILED DESCRIPTION

Figure 1:
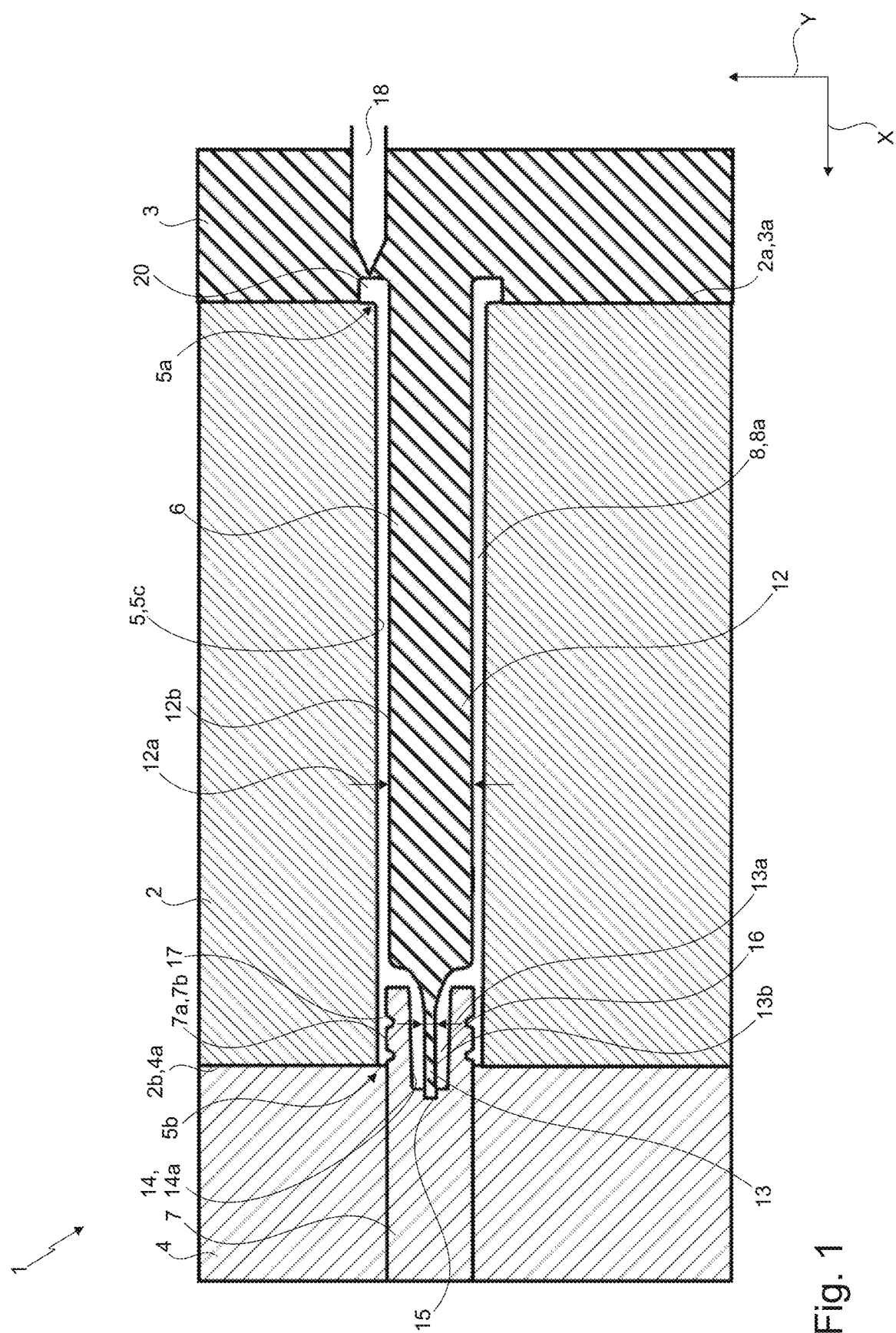
FIG. 1 is a sectional view of the injection moulding tool.
Figure 2:
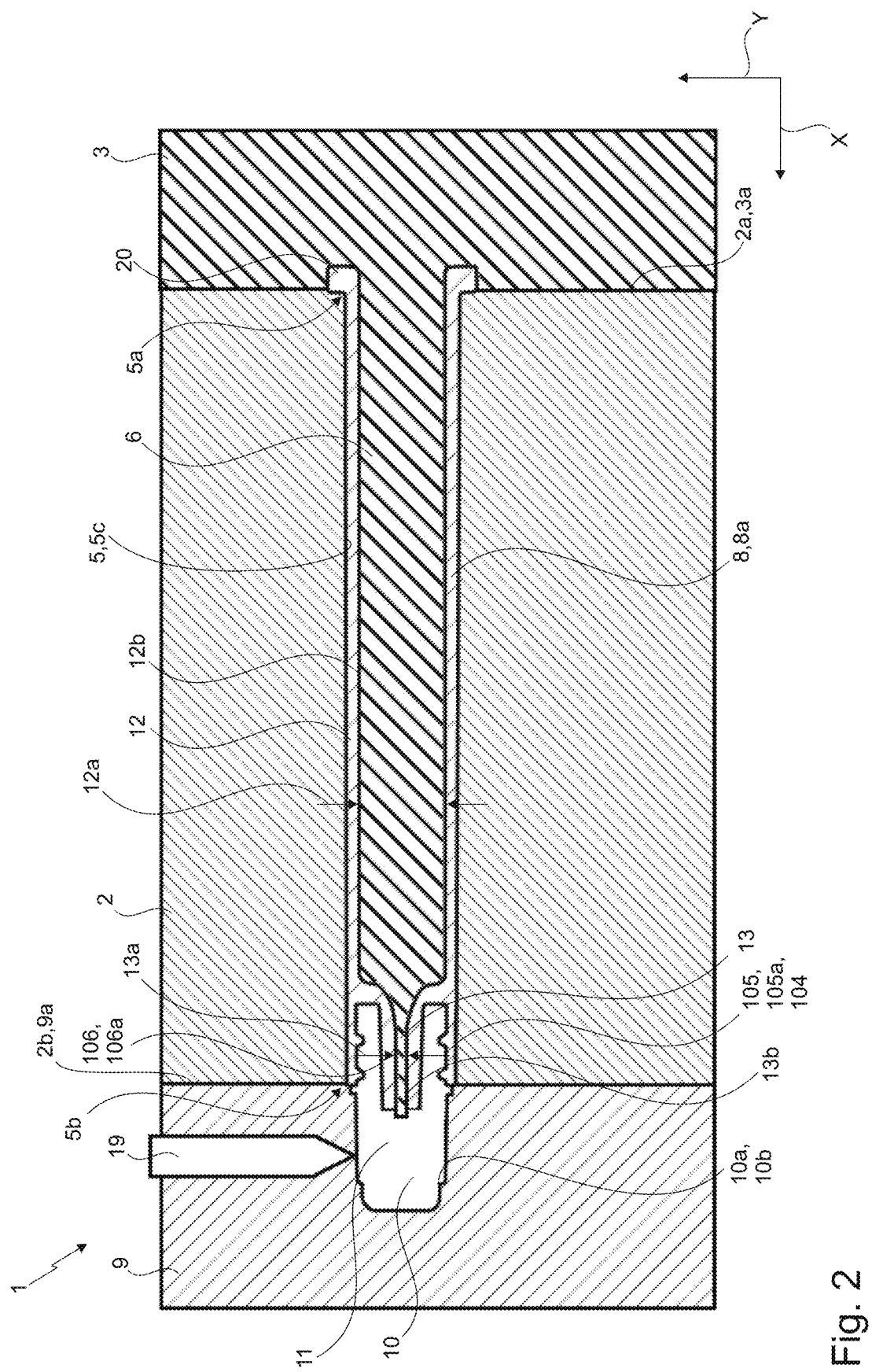
FIG. 2 is another sectional view of the injection moulding tool.
Figure 3:
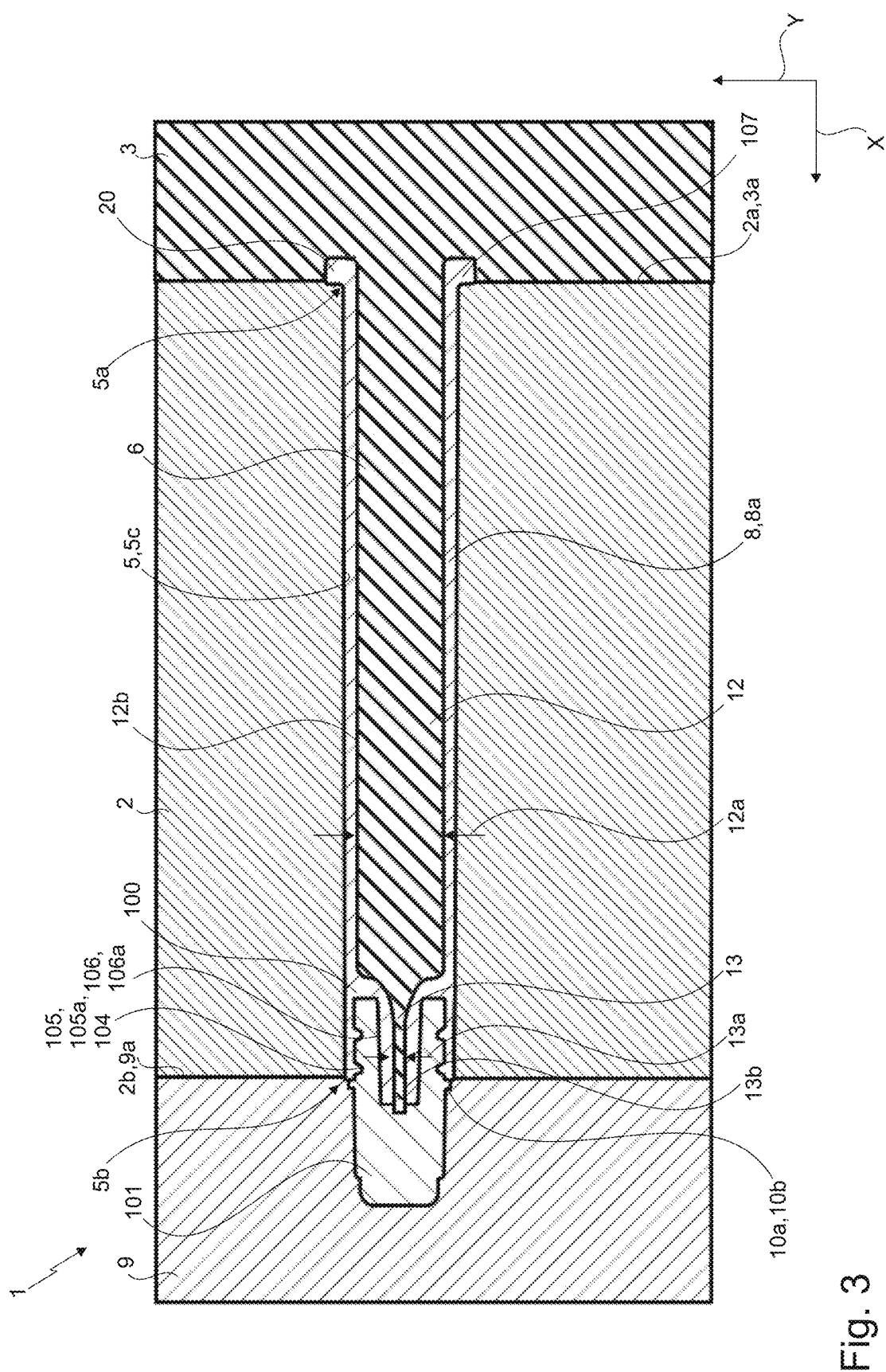
FIG. 3 is another sectional view of the injection moulding tool.

In FIGS. 1 to 3, the injection moulding tool is shown in principle in various phases of the injection moulding process according to the invention for producing a syringe (100) having an integrated closure element (101).

In process step a), the injection moulding tool (1) is provided which comprises a first (2), a second (3) and a third tool portion (4), wherein the first tool portion (2) has a mould cavity (5) open at both sides extending along an axial direction (X), and wherein the second tool portion (3) has a first injection moulding core (6) and the third tool portion (4) has a second injection moulding core (7).

In process step b), the injection moulding tool (1) is closed such that the first tool portion (2) contacts the second (3) and third tool portion (4), and the first (6) and second injection moulding core (7) each enter the mould cavity (5) of the first tool portion (2) through an opening (5a, 5b) and finally contact each other, as a result of which these tool portions (2, 3, 4) form a first cavity (8).

In process step c), a first plastic material is injected into the first cavity (8), as a result of which a hollow cylindrical syringe body (102) is formed with an end region (103) at its distal end (102a), wherein the end region (103) has an attachment element (105) provided with an inner thread (104) and a hollow cylindrical end piece (106) which is at least partially bordered by the attachment element (105).

In process step d), the tool portions (2, 3, 4) are cooled, as a result of which the syringe body (102) cools and hardens.

In process step e), the first tool portion (2) is brought into contact with a fourth tool portion provided with a mould cavity (9) closed on one side, as a result of which a second cavity (11) is formed at the distal end (102a) of the syringe body (102). This is shown in FIG. 2.

In process step f), a second plastic material is injected into the second cavity (11), as a result of which the closure element (101) is integrally formed on the attachment element (105), wherein the first and the second plastic material do not enter into a cohesive connection.

Finally, in FIG. 3 the syringe (100) is shown with the integrated closure element (101) in the injection moulding tool. The closure element (101) and the syringe body (102) are further cooled and thus harden. The fourth tool portion is then removed and the syringe (100) with the integrated closure element (101) can be ejected.

The mould cavity (5) of the first tool portion (2) has a longitudinal extension along the axial direction (X) and a height extension along a second direction (Y). This mould cavity (5) is also formed to be hollow cylindrical with a circular base. Moreover, the mould cavity (5) of the first tool portion (2) has a first opening (5a) into which the first injection moulding core (6) enters in process step b), and a second opening (5b) into which the second injection moulding core (6) enters in process step b).

The first (6) and second injection moulding cores (7) also have a longitudinal extension along the axial direction (X). Furthermore, these are designed cylindrically. The first injection moulding core (6) comprises a first cylindrical portion (12) with a first diameter (12a) and a second cylindrical portion (13) with a second, smaller diameter (13a). Here, the first (12) and the second cylindrical portions (13) are adjacent in the axial direction (X).

An inner wall (5c) of the mould cavity (5) of the first tool portion and an outer wall (12b) of the first cylindrical portion (12) of the first injection moulding core (6) have a first portion (8a) of the first cavity (8) by means of which the hollow cylindrical syringe body (102) is formed.

The second injection moulding core (7) has a mould cavity (14) open on one side in the axial direction (X) and a recess (15) on an inner wall (14a) bordering the mould cavity (14) in the axial direction (X).

In process step b), the second cylindrical portion (13) of the first injection moulding core is received in part in the recess (15) of the second injection moulding core (7). An outer wall (13b) of the second cylindrical portion (13) and an inner wall (14a) of the mould cavity (14) of the second injection moulding core (7) form the third cavity (16) by means of which the conical end piece (106) is formed. By partially receiving the second cylindrical portion (13) in the recess (15) of the mould cavity (14), the second cylindrical portion (13) projects beyond the inner wall (14a). This configuration ensures that no first plastic material enters the channel (108) of the end piece (106) and thus closes it.

The attachment element (101) provided with the inner thread (104) is formed by means of a fourth cavity (17). This fourth cavity (17) is formed by the outer region (7a) of the second injection moulding core (7) and the inner wall (5c) of the mould cavity (5) of the first tool portion (2). This outer region (7a) of the second injection moulding core (7) has recesses and protrusions (7b), by which the inner thread (104) is formed on the attachment element (101).

The second tool portion (3) having the first injection moulding core (7) is designed to be T-shaped in part. Both the first (2) and the second tool portions (3) have end faces (2a, 3a) that extend along the second direction (Y). After process step b), these end faces (2a, 3a) firmly abut one another. The first cavity (8) or the first opening (5a) of the mould cavity (5) are therefore closed in the axial direction (X) by the second tool portion (3). The second tool portion (3) further comprises a recess (20) that is open to the first cavity (8) and by means of which a finger rest (107) is formed at the proximal end (102b) of the syringe body (102).

The first plastic material is injected through a first injection nozzle (18) arranged in the second tool portion (3). This first injection nozzle (18) is connected to the recess (20). The first plastic material is therefore injected into the first cavity (8) through this recess (20).

The third tool portion (4) having the second injection moulding core (7) is likewise designed to be T-shaped in part. Both the first (2) and the third tool portions (4) have end faces (2b, 4a) that extend along a second direction (Y). After process step b), these end faces (2b, 4a) firmly abut one another and the first cavity (8) or the second opening (5b) of the injection mould cavity (5) are thus closed in the axial direction by the third tool portion (4). The second injection moulding core (7) is thus arranged rotatably in a bore of the third tool portion (4). The second injection moulding core (7) can thus be demoulded between process steps d) and e) by a rotational movement of the attachment element (105) or of the inner thread (104) of the syringe body (102).

After the demoulding of the second injection moulding core (7) and removal of the third tool portion (4), the first tool portion (2) contacts the fourth tool portion (9). The end faces (2b) of the first tool portion (2) therefore firmly abut corresponding end faces (9a) of the fourth tool portion (9). As is visible in FIG. 2, the end piece (106) made in process step c) projects over the end faces (2b) of the first tool portion (2) and into the mould cavity (14) of the fourth tool portion (9).

The second cavity (11) formed in process step e) is formed by an inner wall (14a) of the mould cavity (14) of the fourth tool portion (9) and by outer regions of the end region (103) of the syringe body (102). These outer regions are the outer wall (106a) of the end piece (106) and the inner wall (105a) of the attachment element (105) or the inner thread (104) of the attachment element (105).

Recesses and/or protrusions (10b) are arranged on the inner wall (10a) of the mould cavity (10) of the fourth tool portion (9) such that the closure element (101) is formed with corresponding protrusions (101a) such as longitudinal ribs. Such protrusions are shown in FIG. 9.

The second plastic material is injected into the second cavity (11) through a second injection nozzle (19). This second injection nozzle (19) is arranged in the fourth tool portion (9) and is connected to the mould cavity (10) of the fourth tool portion (9).

Figure 4:
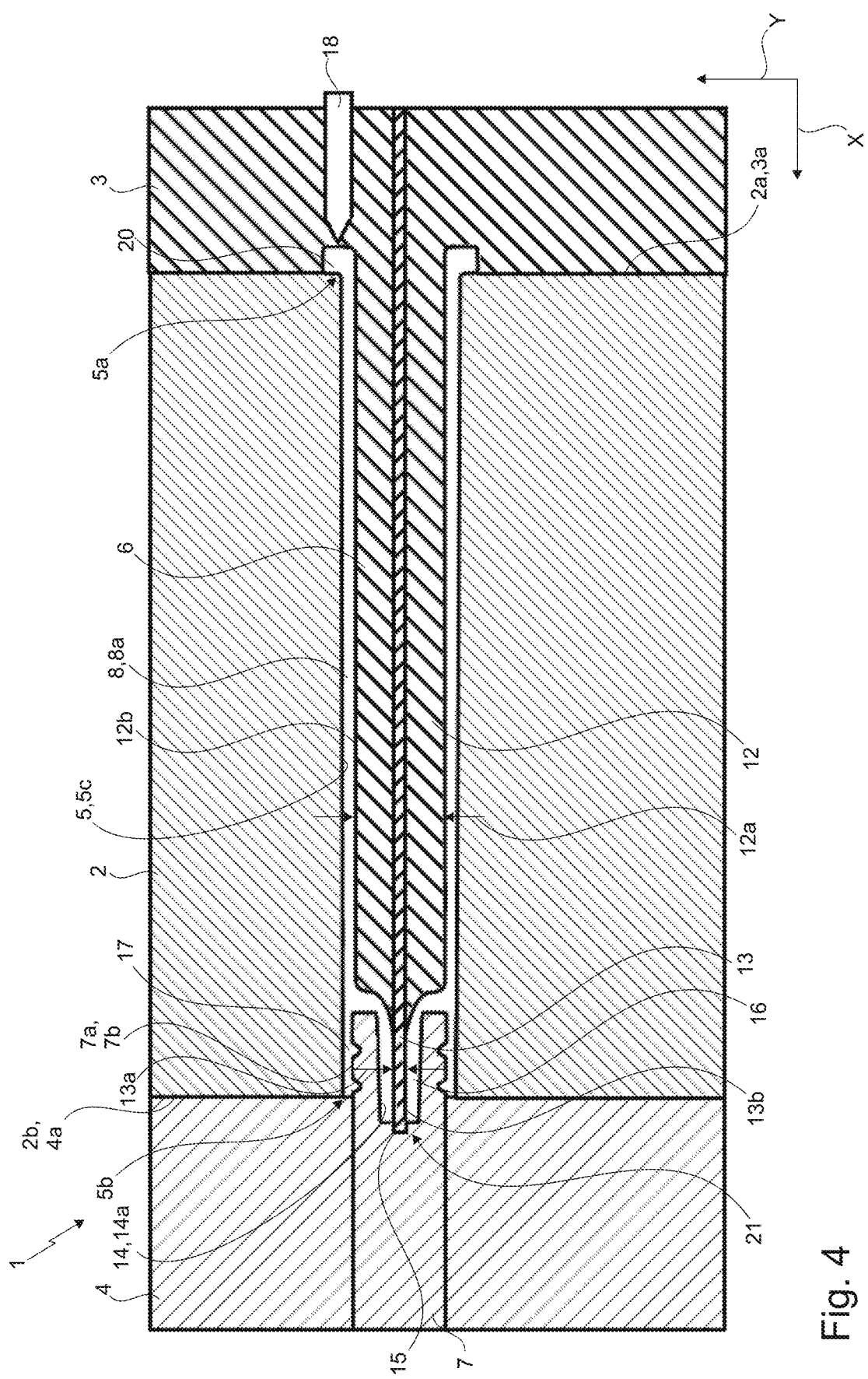
FIG. 4 is a sectional view of the injection moulding tool according to another embodiment.
Figure 5:
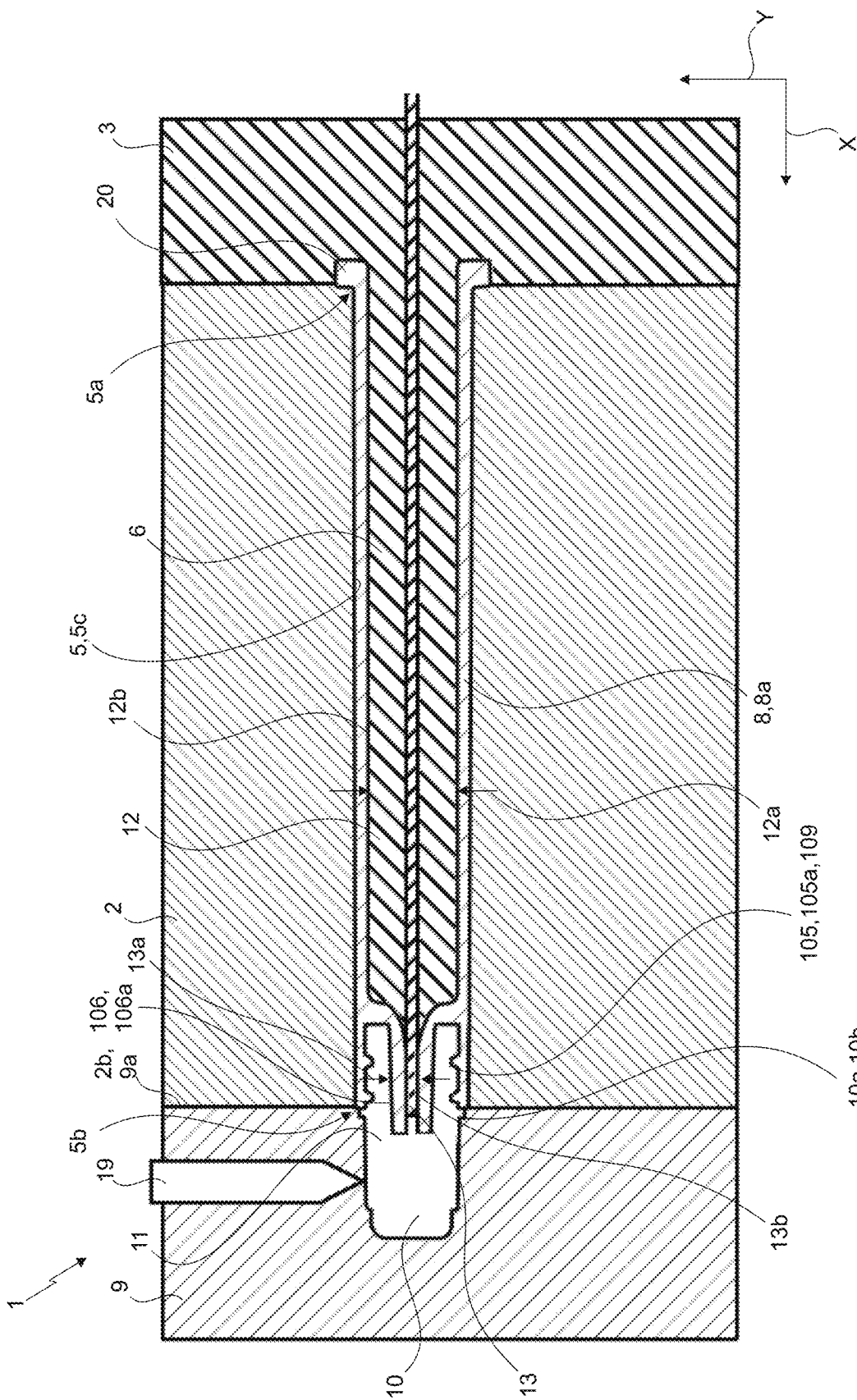
FIG. 5 is a sectional view of the injection moulding tool according to another embodiment.

In FIGS. 4 and 5, an injection moulding tool is shown according to another embodiment. In this case, the first injection moulding core (6) is designed telescopically, wherein the second cylindrical portion (13) is displaceable relative to the first portion (12).

In process steps b) to d), the second cylindrical portion (13) is in a maximum axial position (21) such that the second cylindrical portion (13) contacts the second injection moulding core (7). Between process steps d) and e), however, the second cylindrical portion (13) is displaced in the axial direction (X) away from the third tool portion (4). A portion of the inner channel (108) of the end piece (106) is thus released, so that in the next process step f), the second plastic material enters the channel (108) of the end piece (106). This entered plastic material represents a sealing of the channel (108) or a sealing portion (110) of the closure element (101). A correspondingly produced syringe (100) is shown in FIG. 8.

The telescopic design is realised in that a cylindrical rod-shaped element is arranged in a centrally arranged through-hole in the first injection moulding core (6). This cylindrical rod-shaped element comprises the second cylindrical portion (13) of the first injection moulding core (6) and can be shifted relative to the first cylindrical portion in an axial direction (X). This can be achieved for example by a drive.

FIGS. 6 to 9 show corresponding embodiments of syringes (100) having an integrated closure element (101).

The prefillable syringes (100) shown are suitable for medical applications and comprise a hollow cylindrical syringe body (102) at the distal end (102a) of which an end region (103) is arranged. The end region (103) comprises an attachment element (105) provided with an inner thread (104) and a hollow cylindrical end piece (106) at least partially bordered by the attachment element (105).

The end piece (106) has an inner channel which has a smaller inner diameter (106b) than the inner diameter (102c) of the syringe body (102). In addition, the outer diameter (102d) of the syringe body (102) is greater than the outer diameter (106c) of the end piece (106). The end piece (106) in this embodiment is formed as a cone, the outer diameter (106b) of which tapers continuously. A shallow slope between 4% and 8% is preferred here. Particularly preferably, the cone is formed according to ISO 594 with a slope of 6% and thus constitutes a male luer cone. However, other shapes of the end piece are also conceivable.

In this case, the end piece (106) is surrounded centrally by the attachment element (105). In addition, the length of the end piece (106) along the longitudinal axis $X_1$ is greater than the length of the attachment element (105) along the longitudinal axis $X_1$, so that the end piece (106) projects beyond the attachment element (105). By means of such an arrangement, a connection can be locked between the syringe (100) and, for example, a transfer system (not shown here) and secured against inadvertent loosening. Preferably, the end piece and the attachment element (105) are configured according to ISO 594, as a result of which a luer lock system is realised.

In FIGS. 7 and 8, the syringe (100) is provided with a piston (109). In this case, in the cavity of the syringe body (102), a piston (109), also called a plunger stopper or stopper, is movably arranged along a longitudinal direction ($X_1$). In this case, at least the outer surface of the piston (109) is made of a resilient material so that the piston lies sealingly against an inner wall of the hollow cylindrical syringe body. The piston (109) at its proximal end has a threaded blind bore (109a), into which in an application a piston rod with a head-side thread can be screwed. Alternatively, instead of a screw connection other connection types, such as plug connections, are also conceivable. Furthermore, the piston (109) is conically tapered or pointed at its distal end in the distal direction ($X_1$). Specifically in prefilled syringes, it is particularly important that the piston rests in a sufficiently sealing manner on the inner wall of the syringe body (102) as an undesired leakage of the medium (drug) located in the cavity should be prevented. Similarly, entry of impurities into the syringe is undesirable. At the same time, however, a comfortable, smooth displacement of the piston (109) must be possible in order to convey the medium through the channel of the end piece (106) out of the syringe (100). For this purpose, the inner walls of the syringe body (102) are usually coated or siliconised. The resilient material of the piston must also be compatible with the type of sterilisation selected.

Such prefillable syringes (syringe bodies) are manufactured, packaged and sterilised under clean room conditions by the primary packaging manufacturer and delivered ready for filling directly to the clean room of the filler, for example a pharmacist, and can be used for filling without further treatment steps. The prefillable syringes are filled by the filler from the proximal side or the flange side. To make this possible, the distal end of the syringe (100) or the end piece (106) must be sealed beforehand by means of the closure element (101).

After the syringe body (102) with the closure element (101) according to the invention has been filled with the medium by the filler at the proximal end or the flange side, the piston (109) is inserted. The piston (109) is compressed by a gripper in the radial direction and is introduced into the filled syringe body (102) on the flange side.

In FIG. 8, an embodiment of a syringe (100) having an integral closure element (101) is shown wherein the closure element (101) has a sealing portion (110). This sealing portion (110) projects into the inner channel (108) of the end piece (106) and thus seals this channel (108). Because the first plastic material of the syringe body (102) and the second plastic material of the closure element (101) do not enter into a cohesive connection, the sealing portion (110) with the closure element (101) is detachable from the channel (108) or from the syringe body (102).

FIG. 9 is a side view of the closure element (101) arranged on the syringe body (102). The closure element (101) is circular cylindrical and has on its surface longitudinal ribs and a radially encircling rib.

In FIGS. 10 to 15, the injection moulding tool is shown in principle in various phases of the injection moulding process according to the invention for manufacturing a syringe (100) having an integrated closure element (101) and protrusions (111) arranged on the closure element.

Figure 10:
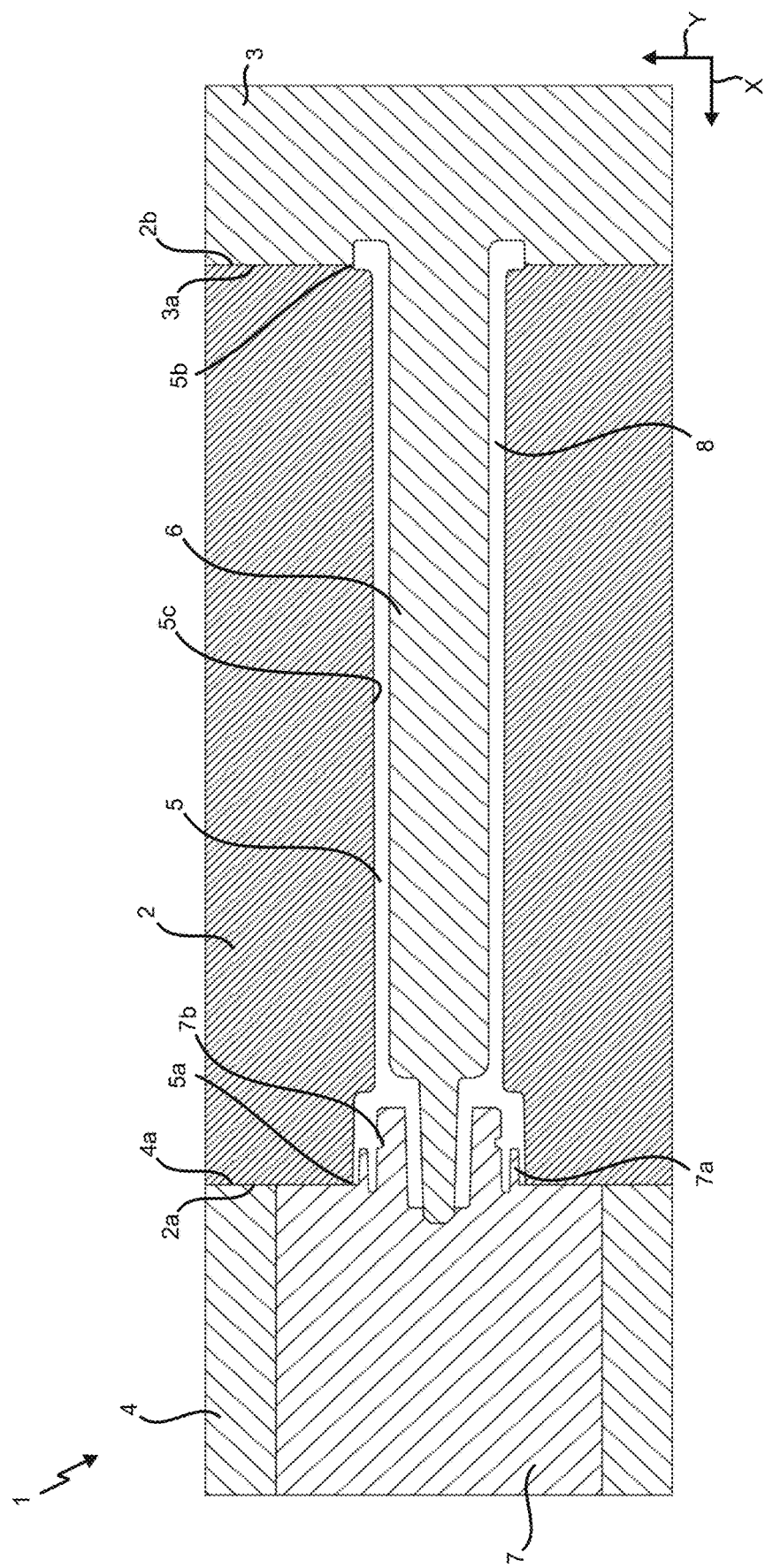
FIG. 10 is a sectional view of the injection moulding tool.

FIG. 10 shows an injection moulding tool (1) which comprises a first (2), a second (3) and a third tool portion (4). The first tool portion (2) has a mould cavity (5) open at both sides in the first axial direction (X). The second tool portion (3) has a first injection moulding core (6) that penetrates through an opening (5b) into the mould cavity (5). The injection moulding core (6) extends in the first axial direction (X) through the entire mould cavity (5) and is configured rotationally symmetrically in the form of a syringe. The third tool portion (4) likewise has an injection moulding core (7). This injection moulding core (7) likewise penetrates through an opening (5b) into the mould cavity (5). The injection moulding core (7) inter alia has protrusions (7a) and depressions (7b). The protrusions (7a) form recesses (112) on the attachment element (105). An inner thread is formed on the attachment element (105) through the depressions (7b) on the injection moulding core (7).

Figure 11:
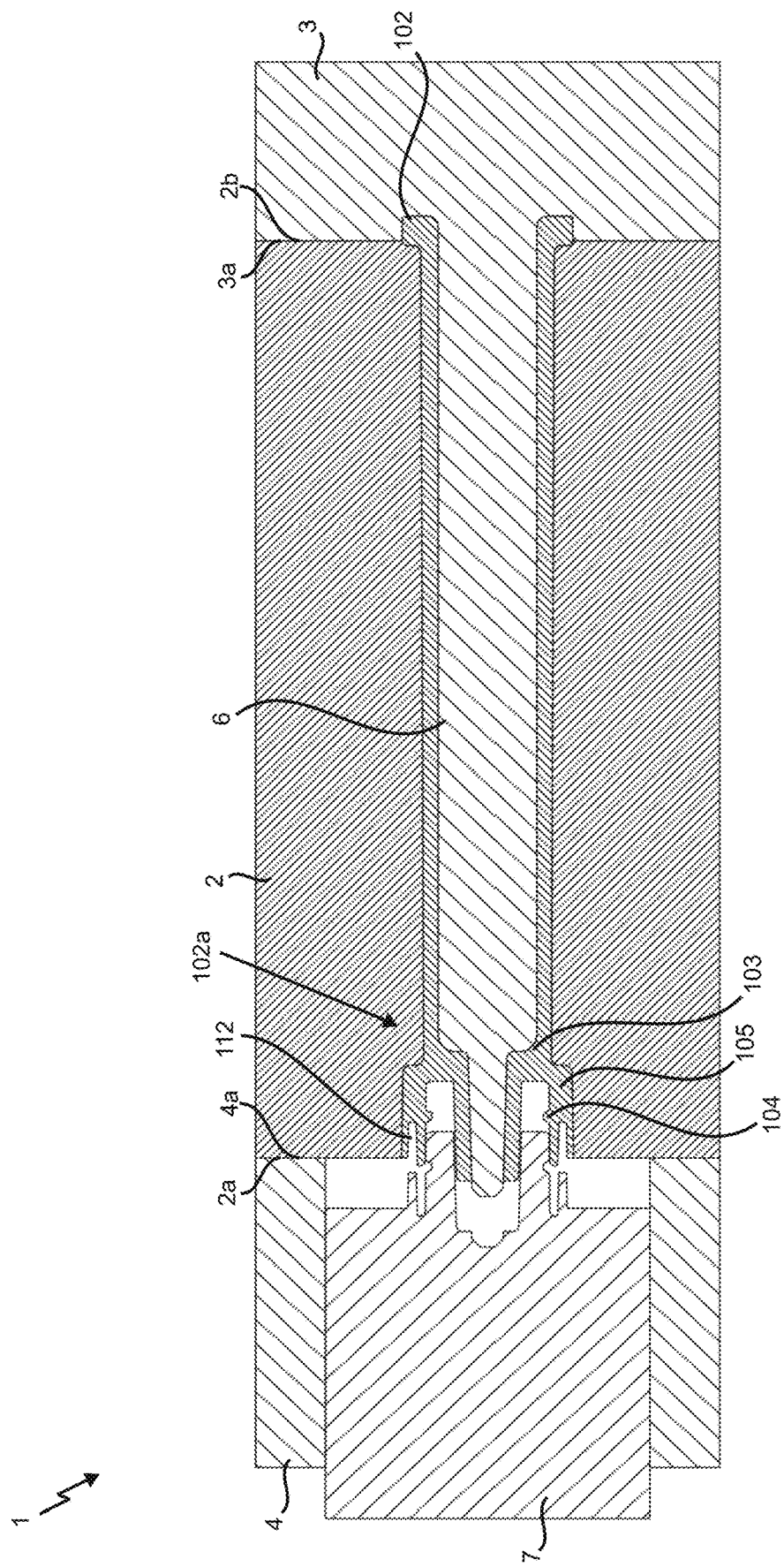
FIG. 11 is another sectional view of the injection moulding tool.

FIG. 11 accordingly shows an injection moulding tool (1) according to process step b), since the tool portions (2, 3, 4) and the injection moulding cores (6, 7) already contact each other. In this case, a first end face (2a) of the first tool portion (2) and an end face (4a) of the third tool portion (4), as well as the second end face (2b) of the first tool portion (2) and an end face (3a) of the second tool portion (3), contact each other. As a result of the various elements contacting each other, a first cavity (8) is formed.

Figure 12:
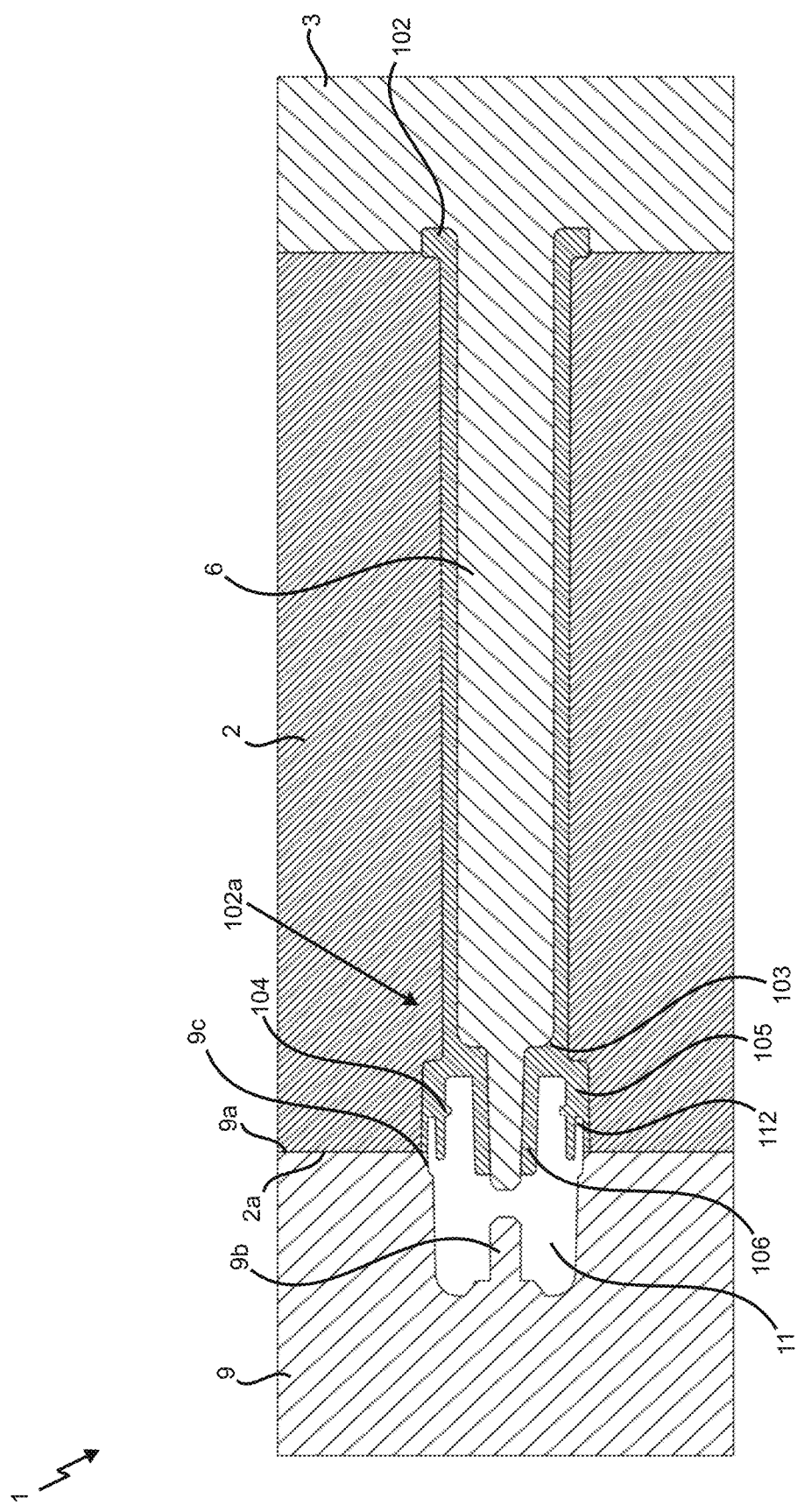
FIG. 12 is another sectional view of the injection moulding tool.

FIG. 12 shows an injection moulding tool (1) after completion of process steps c) and d). In this drawing, a hollow cylindrical syringe body (102) is already formed that, at its distal end (102a), has an end region (103) comprising an attachment element (105). This attachment element (105) has an inner thread (104) and a recess (112). This means that the first cavity (8) is already completely filled with the first plastic material, and the shaped syringe body (102) touches the inner wall (5c) of the mould cavity (5) on one side, wherein contact is made on the opposite side of the injection moulding core (6). As also shown in FIG. 2, the injection moulding core (7) of the third tool portion (4) is demoulded by the syringe body (102), wherein the injection moulding core (7) must perform a rotational movement in order to be loosened from the formed inner thread (104) and the recesses (112) without damaging these components.

Figure 13:
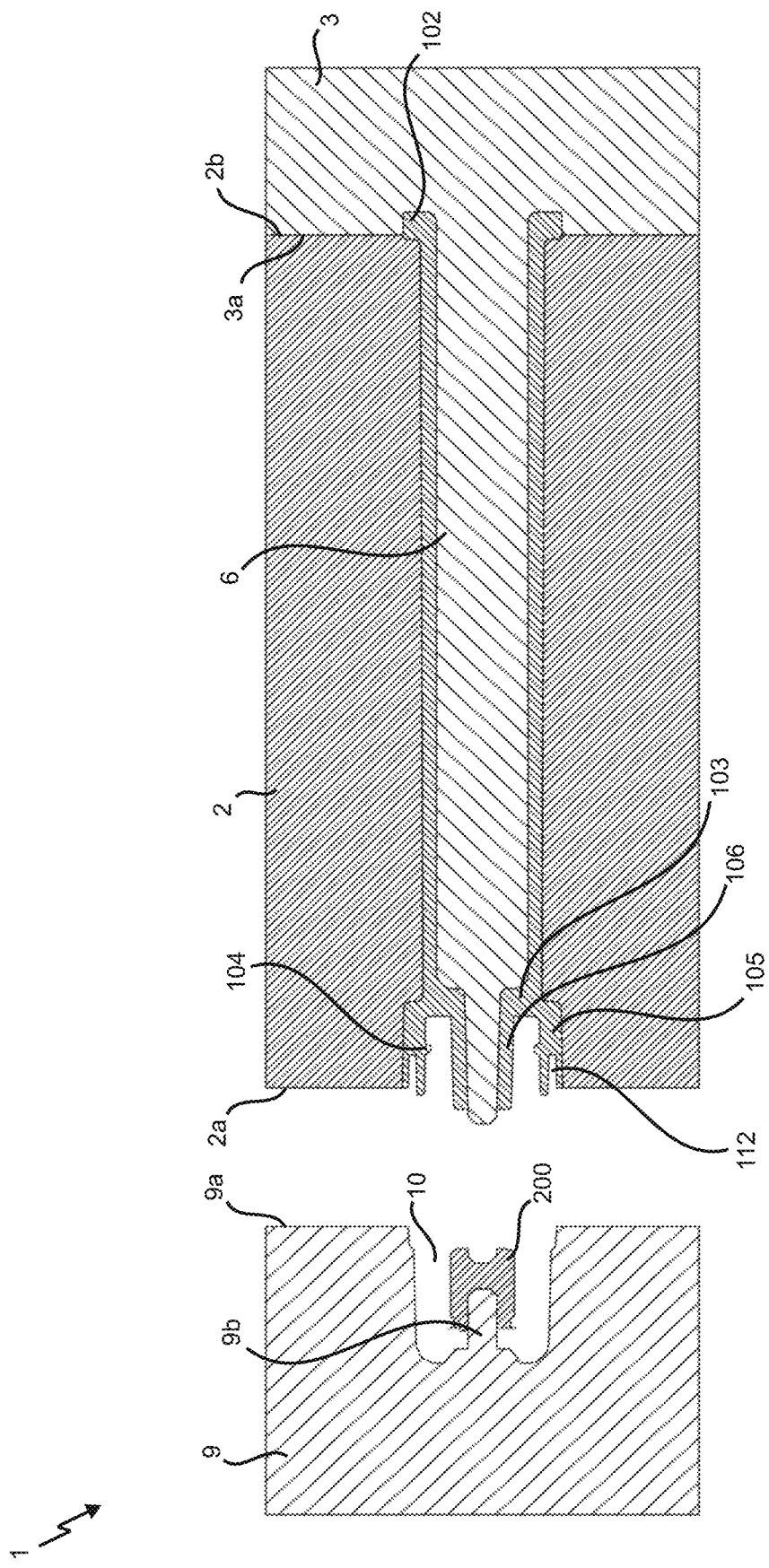
FIG. 13 is a sectional view of the injection moulding tool of a preferred embodiment.

FIG. 13 shows another sectional view of the injection moulding tool (1). A fourth tool portion (9) in this case has already been brought into contact with the first tool portion (2). The end face (9a) of the fourth tool portion (9) and the first end face (2a) of the first tool portion (2) contact each other and form a second cavity (11). The cavity (11) is formed inter alia by the mould cavity (10) of the fourth tool portion (9) and the recesses (112) of the attachment element (105). In this view, the syringe body (102) is already formed and on its distal end (102a) has a first end region (103) with an attachment element (105), wherein the attachment element (105) comprises an inner thread (104) and recesses (112). This fourth tool portion (9) additionally has a holding element (9b). When the second plastic material is injected into the second cavity (11), a closure (101) on the attachment element (105) is now integrally formed, the hollow cylindrical end piece (106) being closed by the second plastic material in this embodiment.

Figure 14:
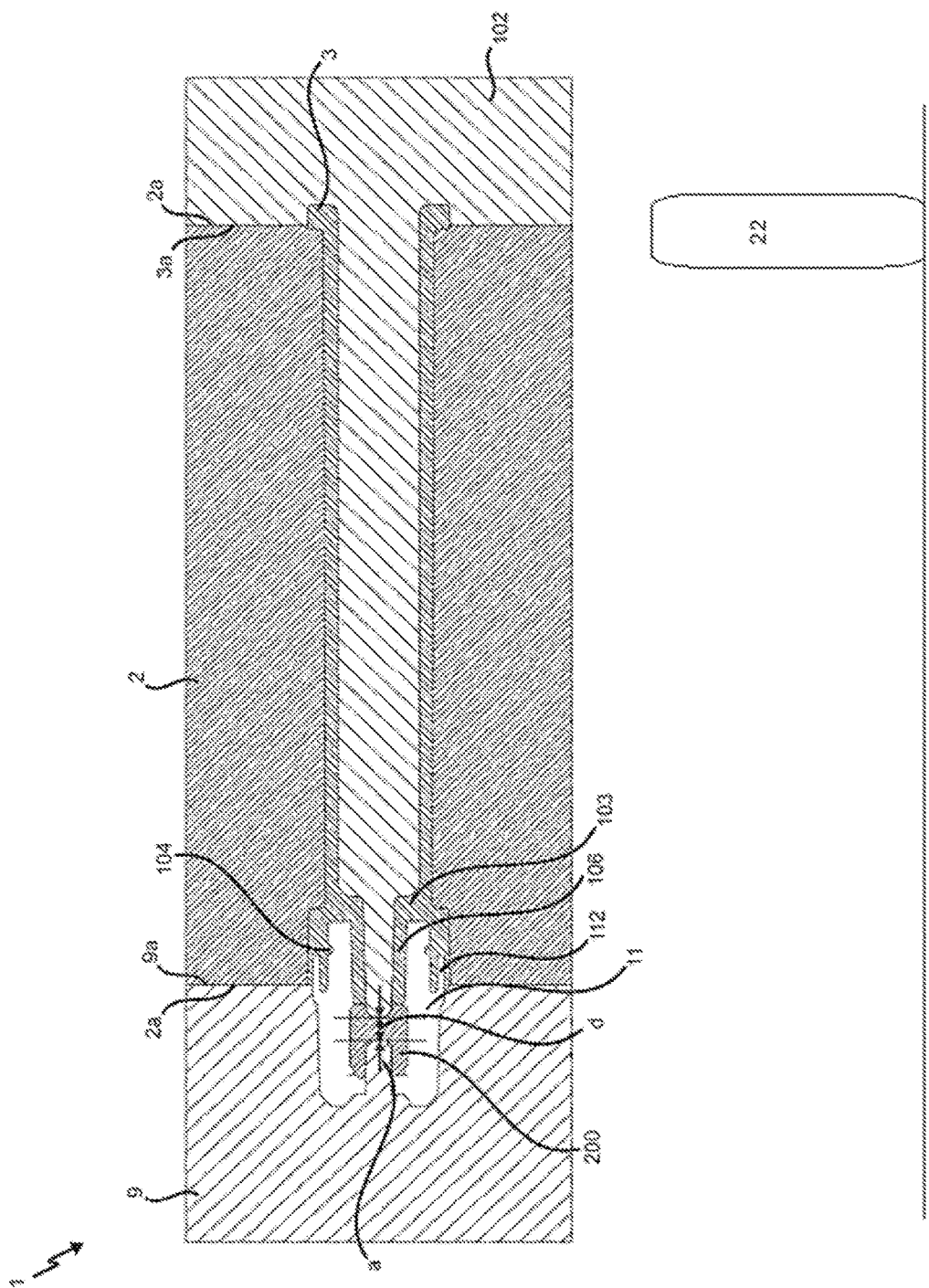
FIG. 14 is another sectional view of the injection moulding tool of the preferred embodiment according to FIG. 3.

FIG. 14 is a sectional view of the injection moulding tool (1) for manufacturing a syringe (100) according to a preferred embodiment. In this view, the syringe body (102), as also shown in FIG. 3, is already formed after completion of process steps a)-d). Now, as in FIG. 3, a fourth tool portion (9) is provided that has a holding element (9b) on which, in this preferred embodiment, a sealing element (200) is mounted, in particular plugged. Now, the end face (9a) of the fourth tool portion (9) is brought into contact with the first end face (2a) of the first tool portion (2). Also shown is an optional heating and cooling means (22) able to individually heat and cool the different tool portions.

Figure 15:
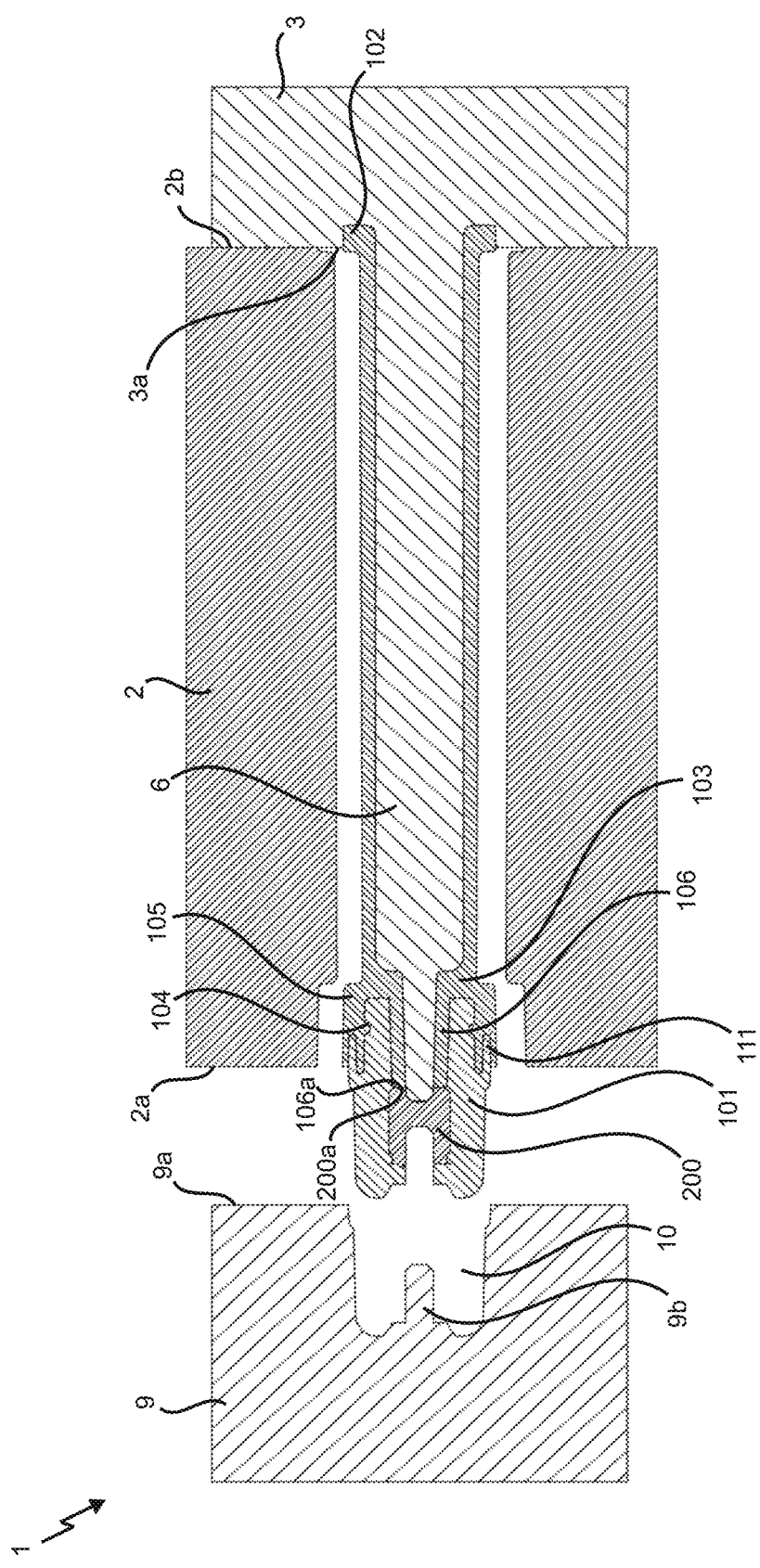
FIG. 15 is another sectional view of the injection moulding tool of the preferred embodiment according to FIG. 3.

FIG. 15 is a further sectional view of the injection moulding tool from FIG. 4, wherein in this view, the end faces (2a, 9a) already contact each other and, with the injection moulding core (6) of the second tool portion (3) and the formed syringe body (102), thus form a second cavity (11). Upon contact of the end faces (2a, 9a), the sealing element (200) is firmly pressed against the hollow cylindrical end piece (106) of the syringe body (102). The distance (a) in the first axial direction (X) between the holding element (9b) and the end of the first injection moulding core (6) is less than or equal to the thickness (d) of the sealing element (200). The end face (200a) of the sealing element (200) and the end face (106a) of the hollow cylindrical end piece (106) thus contact each other. The second plastic material can then be injected into the second cavity (11). In contrast to the previous embodiment without a sealing element (200), the hollow cylindrical end piece (106) is now sealed by the sealing element (200) and not by the second plastic material.

Figure 16:
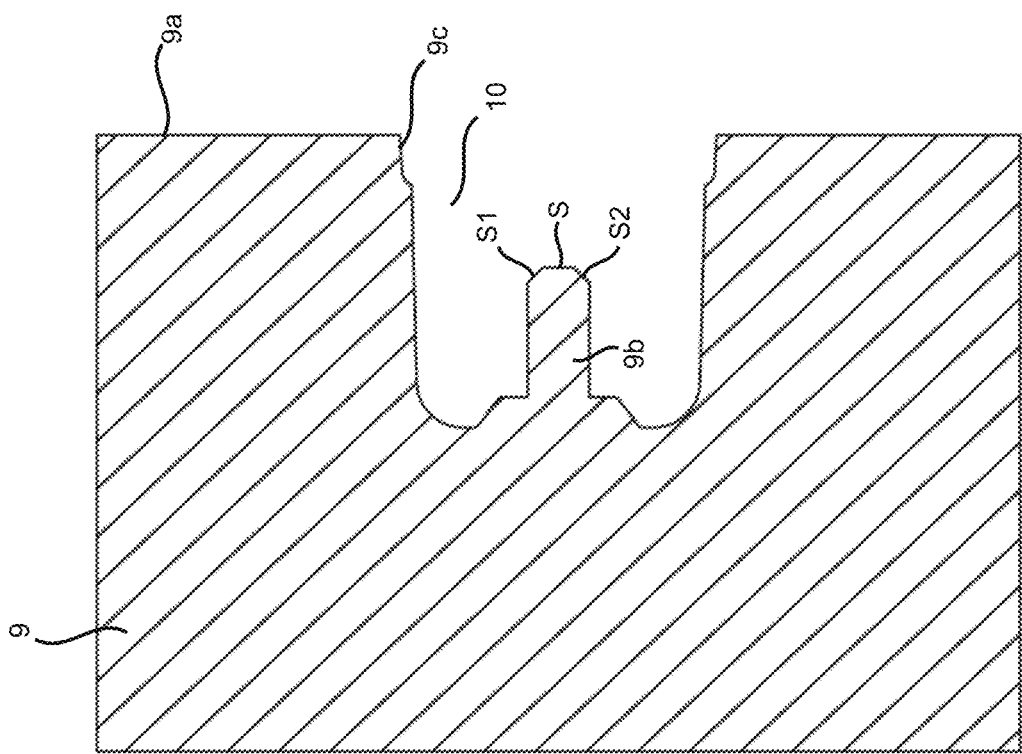
FIG. 16 is a sectional view of the fourth tool portion.

FIG. 16 is a further sectional view of the injection moulding tool (1) of a preferred embodiment after completion of the process. In this view, the first tool portion (2) and the fourth tool portion (9) are demoulded from the syringe (100) so that the syringe (100) can be removed, wherein the syringe (100) is withdrawn from the second tool portion (3) during the removal.

Figure 17:
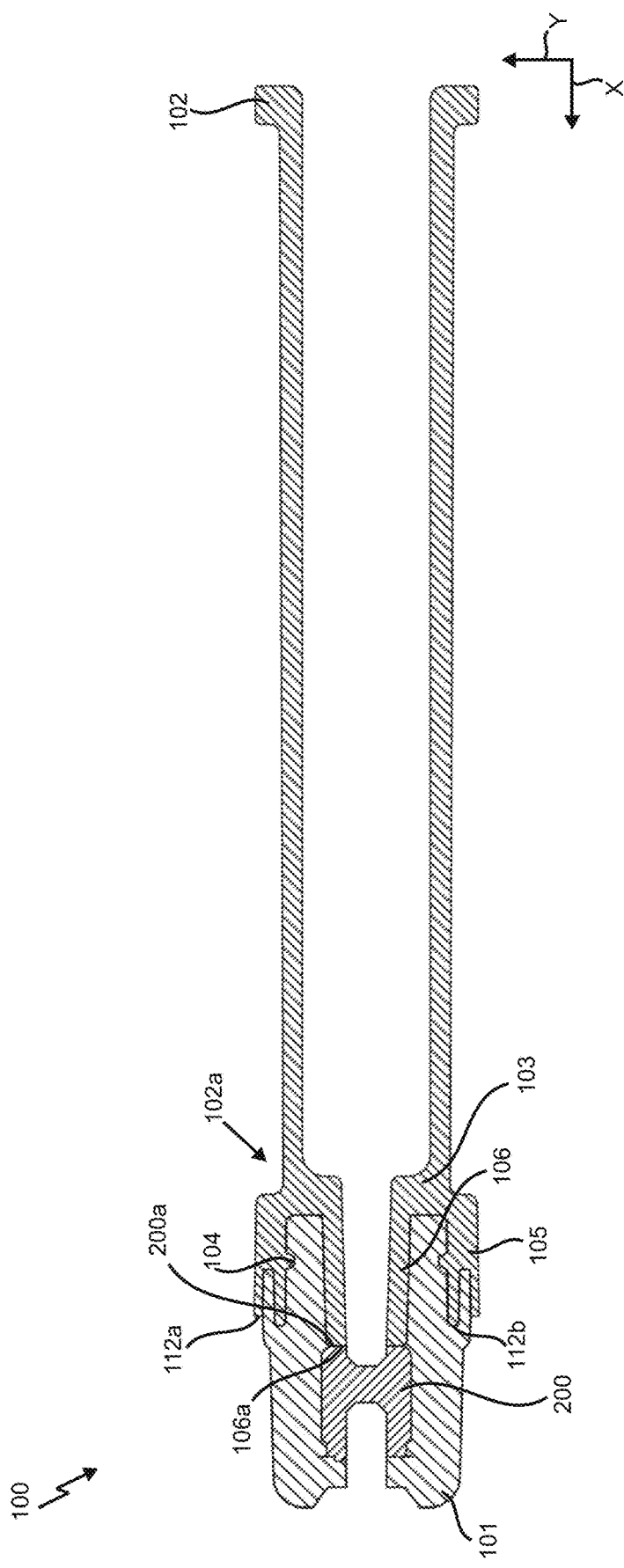
FIG. 17 is a sectional view of a syringe of the preferred embodiment according to FIG. 3.

FIG. 17 is a sectional view of the fourth tool portion (9). This tool portion (9) has an end face (9a) and a holding element (9b). The holding element projects into the mould cavity (10) of the fourth tool portion (9). In a preferred embodiment, a sealing element (200) can be mounted on this holding element (9b). In this tool portion (9), the holding element (9b) could also be dispensed with if no sealing element (200) should be present in the syringe (100). The tool portion (9) also has depressions (9c), by means of which the mould halves (9) are adapted to the shape of the syringe body (102), and thus the protrusions (111) of the closure element (101) can be formed by the recesses (112) when the second plastic material is injected. In addition, the holding element (9b) and the sealing element (200) are designed to be substantially rotationally symmetrical. The holding element (9b) on a front side (S) has a first bevel (S1) and a second bevel (S2), which taper the holding element (9b) in an end region and by which the mounting and positioning of the sealing element (200) on the holding element (9b) are facilitated.

Figure 18:
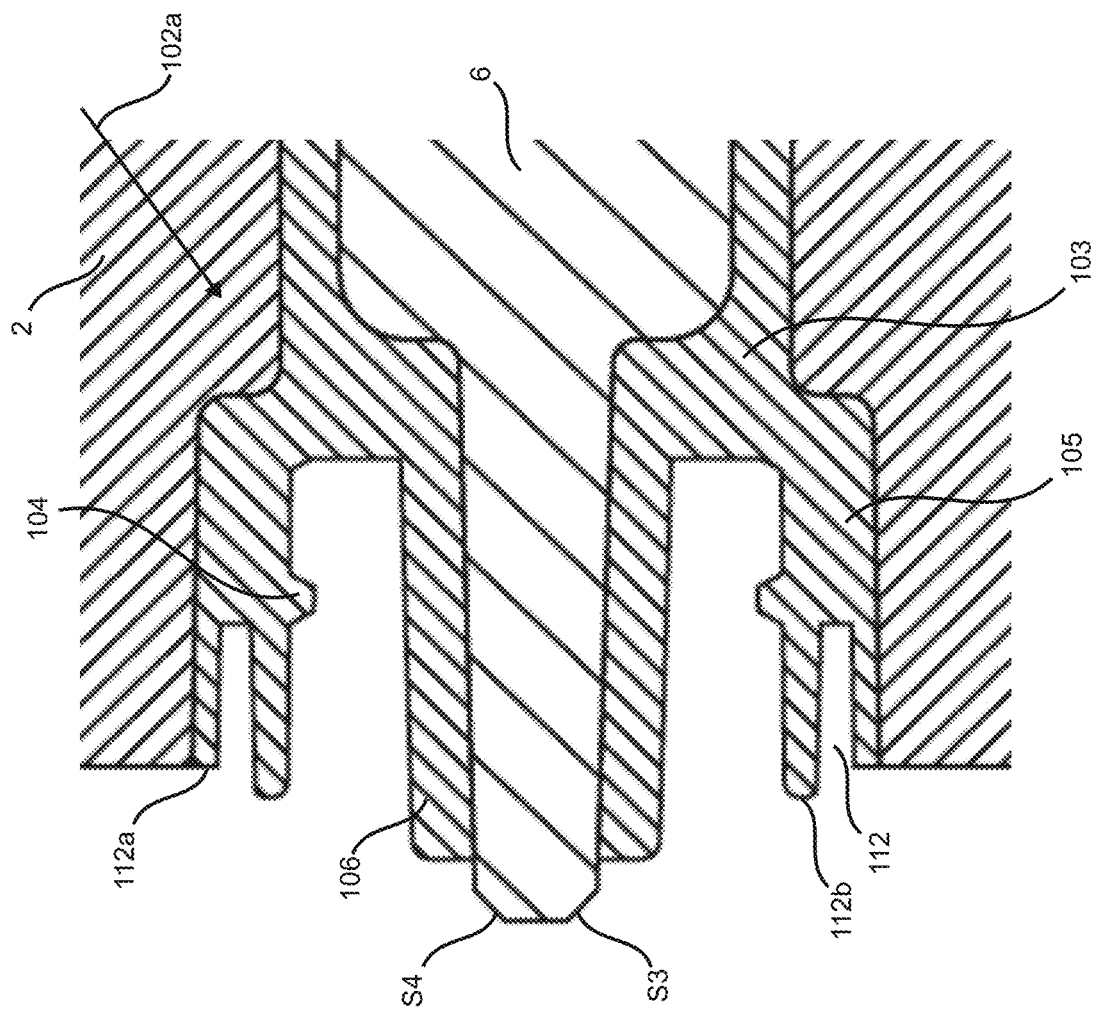
FIG. 18 shows an enlarged detail of the distal end of the syringe body from FIG. 3.

FIG. 18 is a sectional view of a syringe (100) according to a preferred embodiment produced by the aforementioned method. A hollow cylindrical syringe body (102), which can now be filled, was formed by the injection moulding process. This syringe body (102) has at its distal end (102a) an end region (103) that comprises an attachment element (105). As already mentioned, an inner thread (104) and recesses (112) are formed on this attachment element (105). Protrusions (111) of the closure element (101) now engage these recesses (112). A sealing element (200) is also provided, which is enclosed by the second plastic material such that a sealing of the hollow cylindrical end piece (106) from the environment is still ensured.

Figure 19:
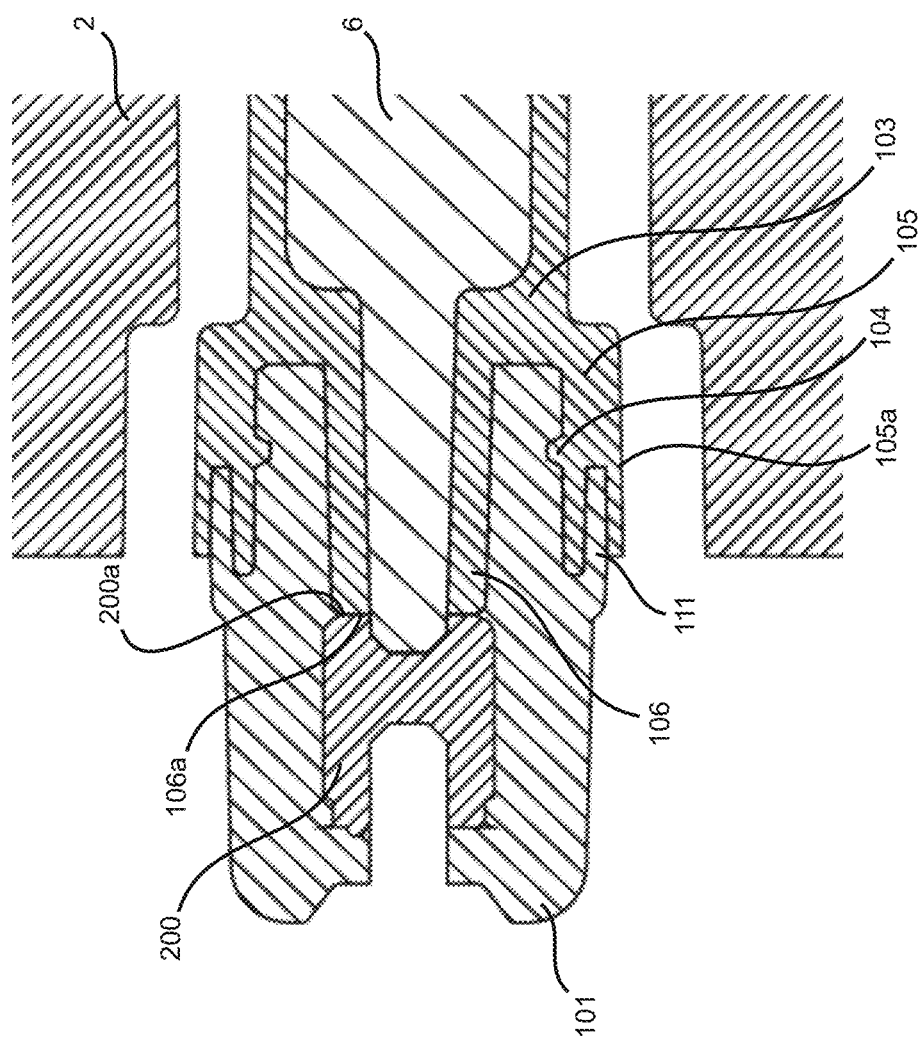
FIG. 19 shows an enlarged detail of the distal end with closure element according to FIG. 5.

FIG. 19 shows an enlarged detail of the distal end (102a) of the syringe body (102). Here it can be seen in particular that the recess (112) is bordered at least in the second axial direction (Y) by an inner (112b) and an outer wall portion (112a). The recess (112) is thus open on one side in a first axial direction (X) and bordered in a second axial direction (Y) by the wall portions (112a, 112b), and thus has a substantially U-shaped cross section. The inner wall portion (112b) extends in the first axial direction (X) farther than the outer wall portion (112a). The second injection moulding core (6) projects over the hollow cylindrical end piece (106) and has a first bevel (S3) and a second bevel (S4) that facilitate the positioning of the sealing element (200) (not shown here).

FIG. 20 likewise shows an enlarged detail of the distal end (102a) of the syringe body (102). In this drawing, the closure element (101) has already been integrally formed on the attachment element (105). The sealing element (200) is still pressed by the closure element (101) formed on the hollow cylindrical end piece (106) of the syringe body (102).

Furthermore, the outer wall portion (112a) forms part of the outer face (105a) of the attachment element (105).

All the features disclosed in the application documents are claimed as essential to the invention provided they are novel over the prior art individually or in combination.

LIST OF REFERENCE SIGNS 1 injection moulding tool
2 first tool portion
2a end face of the first tool portion
2b end face of the first tool portion
3 second tool portion
3a end face of the second tool portion
4 third tool portion
4a end face of the third tool portion
5 mould cavity of the first tool portion
5a first opening of the mould cavity
5b second opening of the mould cavity
5c inner wall of the mould cavity
6 first injection moulding core
7 second injection moulding core
7a outer region of the second injection moulding core
7b protrusions and recesses on the outer region of the second injection moulding core
8 first cavity
9 fourth tool portion
9a end face of the fourth tool portion
10 mould cavity of the fourth tool portion
10a inner wall of the mould cavity of the fourth tool portion
10b recesses and protrusions on the inner wall of the mould cavity of the fourth tool portion
11 second cavity
12 first cylindrical portion
12a first diameter
12b outer wall of the first cylindrical portion
13 second cylindrical portion
13a second diameter
13b outer wall
14 mould cavity of the second injection moulding core
14a inner wall of the mould cavity of the second injection moulding core recess
16 third cavity
17 fourth cavity
18 first injection nozzle
19 second injection nozzle
20 recess of the second tool portion
21 maximum axial position
22 heating and cooling means
100 syringe
101 closure element
102 hollow cylindrical syringe body
102a distal end of the syringe body
102b proximal end of the syringe body
102c inner diameter of the syringe body
102d outer diameter of the syringe body
103 end region
104 inner thread
105 attachment element
106 end piece
106a outer wall of the end piece
106b inner diameter of the end piece
106c outer diameter of the end piece
107 finger rest
108 channel of the end piece
109 piston
109a threaded blind bore of the piston
110 sealing portion
X axial direction
Y second direction
X1 sealing portion
100 syringe
101 closure element
102 syringe body
102a distal end of the syringe body
103 end region
104 inner thread
105 attachment element
105a outer face of the attachment element
106 end piece
106a end face of the end piece
111 protrusion
112 recess on the attachment element
112a outer wall portion of the recess
112b inner wall portion of the recess
200 sealing element
200a end face of the sealing element
a distance between holding element and the first injection moulding core
d thickness of the sealing element
S1 first bevel of the front side of the holding element
S2 second bevel of the front side of the holding element
S3 first bevel of the first injection moulding core
S4 second bevel of the second injection moulding core
X first axial direction
Y second axial direction

The invention claimed is:

1. Injection moulding process for producing a syringe (100) with an integrated closure element (101) comprising the following process steps:
   a) providing an injection moulding tool (1) which comprises a first (2), a second (3) and a third tool portion (4), wherein the first tool portion (2) has a mould cavity (5) open at both sides and extending along an axial direction (X), and wherein the second tool portion (3) has a first injection moulding core (6) and the third tool portion (4) has a second injection moulding core (7);
   b) closing the injection moulding tool (1) such that the first tool portion (2) contacts the second (3) and third tool portion (4), and the first (6) and second injection moulding core (7) each enter the mould cavity (5) of the first tool portion (2) through an opening (5a, 5b) and finally contact each other, as a result of which these tool portions (2, 3, 4) form a first cavity (8);
   c) injecting a first plastic material into the first cavity (8), as a result of which a hollow cylindrical syringe body (102) is formed with an end region (103) at its distal end (102a), wherein the end region (103) has an attachment element (105), provided with an inner thread (104), and a hollow cylindrical end piece (106) which is at least partially bordered by the attachment element (105);
   d) cooling the tool portions (2, 3, 4), as a result of which the syringe body (102) cools and hardens;
   e) bringing the first tool portion (2) into contact with a fourth tool portion provided with a mould cavity (9) closed at one end, as a result of which a second cavity (11) is formed at the distal end (102a) of the syringe body (102);

f) injecting a second plastic material into the second cavity (11), as a result of which the closure element (101) is integrally formed on the attachment element (105), wherein the first and the second plastic material do not enter into a cohesive connection;

wherein the first (6) and the second injection moulding core (7) extend along the axial direction (X), wherein the first injection moulding core (6) comprises a first cylindrical portion (12) with a first diameter (12*a*) and a second cylindrical portion (13) with a second, smaller diameter (13*a*), said first (12) and said second cylindrical portion (13) being adjacent in the axial direction (X), and wherein the second injection moulding core (7) has an additional mould cavity (14) open on one side in the axial direction (X) and a recess (15) on an inner wall (14*a*) bordering the additional mould cavity (14) in the axial direction (X);

wherein, with the contacting of the two injection moulding cores (6, 7) in process step b), the second cylindrical portion (13) of the first injection moulding core (6) is received in part in the recess (15) of the second injection moulding core (7);

wherein, between process steps d) and e), the second cylindrical portion (13) is displaced in the axial direction (X) away from the third tool portion (4), wherein, in the following process step f), the second plastic material enters the channel (108) of the end piece (106), as a result of which a sealing of the channel (108) is created, wherein the first injection moulding core (6) is telescopically designed, wherein the second cylindrical portion (13) of the first injection moulding core (6) is displaced relative to the first portion (12) during process steps b) to d), wherein the second cylindrical portion (13) in process steps b) to d) is in a maximum axial position (21) such that the second cylindrical portion (13) contacts the second injection moulding core (7).

2. Method according to claim 1, characterised in that the end region (103) has an attachment element (105) provided with an inner thread (104) and at least one recess (112).

3. Method according to claim 2, characterised in that by injecting the second plastic material into the second cavity (11), the closure element (101) is integrally formed on the attachment element (105), as a result of which a protrusion (111) is formed in the at least one recess (112).

4. Method according to claim 1, characterised in that in process step b), an inner wall (5*c*) of the mould cavity (5) of the first tool portion (2) and an outer wall (12*b*) of the first cylindrical portion (12) of the first injection moulding core (6) form a first portion (8*a*) of the first cavity (8), by means of which the hollow cylindrical syringe body (102) is formed, wherein a third cavity (16) is formed by the additional mould cavity (14) of the second injection moulding core of (7) and the second cylindrical portion (13) of the first injection moulding core (6), by means of which the end piece (106) is formed, wherein the attachment element (105) provided with the inner thread (104) is formed by means of a fourth cavity (17), which is formed by an outer region (7*a*) of the second injection moulding core (7) and the inner wall (5*c*) of the mould cavity (5) of the first tool portion (2).

5. Method according to claim 1, characterised in that between process steps d) and e), the second injection moulding core (7) is demoulded from the attachment element (105) of the syringe body (102) and the third tool portion (4) is removed from the first tool portion (2), wherein the second injection moulding core (7) is demoulded by a rotational movement of the inner thread (104) of the attachment element (105).

6. Method according to claim 1, characterised in that the first plastic material is injected through a first injection nozzle (18) arranged in the second tool portion (3), and the second plastic material is injected through a second injection nozzle (19) arranged in the fourth tool portion (9).

7. Method according to claim 6, characterised in that the mould cavity (5) of the first tool portion (2) has a first opening (5*a*) into which the first injection mould core (6) enters in process step b), wherein the second tool portion (3) has a recess (20) that is open to the first cavity (8) and by means of which a finger rest (107) is formed at the proximal end (102*b*) of the syringe body (102), wherein the first injection nozzle (18) is connected to this recess (20).

8. Method according to claim 1, characterised in that the first (2), second (3), third (4) and fourth tool portions (9) are individually heated and cooled, wherein the heating takes place by means of a laser and the cooling by means of a coolant, wherein the coolant contains water and/or nitrogen and/or $CO_2$.

9. Method according to claim 1, characterised in that the first and the second plastic material are different materials, wherein the first plastic material is a polymer plastic material, wherein the first plastic material is a polyolefin, wherein the first plastic material is a cyclic olefin polymer (COP) or a cyclic olefin copolymer (COC), and the second plastic material is a thermoplastic elastomer.

10. Method according to claim 1, characterised in that the first and the second plastic material are the same materials, wherein these plastic materials are a polymer plastic material.

11. Method according to claim 2, characterised in that the at least one recess (112) is surrounded by an outer (112*a*) and an inner (112*b*) wall portion, wherein the outer wall portion (112*a*) forms a part of the outer surface (105*a*) of the attachment element (105).

12. Method according to claim 2, characterised in that more than three recesses (112) are formed on the attachment element (105), and protrusions (111) complementary thereto are formed on the closure element (101).

13. Method according to claim 1, characterised in that after step d), in a further process step d2), a sealing element (200) is mounted on the fourth tool portion (9), said fourth tool portion (9) having a holding element (9*b*) projecting into the mould cavity (10) of the fourth tool portion (9) that is designed to hold the sealing element (200).

14. Method according to claim 13, characterised in that the sealing element (200) in process step e) is pressed against the hollow cylindrical end piece (106) of the syringe body (102).

15. Method according to claim 13, characterised in that the sealing element (200) after process step f) is surrounded by the second plastic material, while the sealing element (200) after the demoulding of the fourth tool portion (9) is still pressed against the hollow cylindrical end piece (106) of the syringe body (102).

16. Method according to claim 2, characterised in that between process steps d) and e), the second injection moulding core (7) is demoulded from the attachment element (105) of the syringe body (102) and the third tool portion (4) is removed from the first tool portion (2), wherein the second injection moulding core (7) is demoulded by a rotational movement of the inner thread (104) and the at least one recess (112) of the attachment element (105).

17. An injection moulding process for producing a syringe (100) with an integrated closure element (101) comprising the following process steps:
- a) providing an injection moulding tool (1) which comprises a first (2), a second (3) and a third tool portion (4), wherein the first tool portion (2) has a mould cavity (5) open at both sides and extending along an axial direction (X), and wherein the second tool portion (3) has a first injection moulding core (6) and the third tool portion (4) has a second injection moulding core (7);
- b) closing the injection moulding tool (1) such that the first tool portion (2) contacts the second (3) and third tool portion (4), and the first (6) and second injection moulding core (7) each enter the mould cavity (5) of the first tool portion (2) through an opening (5a, 5b) and finally contact each other, as a result of which these tool portions (2, 3, 4) form a first cavity (8);
- c) injecting a first plastic material into the first cavity (8), as a result of which a hollow cylindrical syringe body (102) is formed with an end region (103) at its distal end (102a),
  wherein the end region (103) has an attachment element (105), provided with an inner thread (104), and a hollow cylindrical end piece (106) which is at least partially bordered by the attachment element (105);
- d) cooling the tool portions (2, 3, 4), as a result of which the syringe body (102) cools and hardens;
- e) bringing the first tool portion (2) into contact with a fourth tool portion provided with a mould cavity (9) closed at one end, as a result of which a second cavity (11) is formed at the distal end (102a) of the syringe body (102);
- f) injecting a second plastic material into the second cavity (11), as a result of which the closure element (101) is integrally formed on the attachment element (105), wherein the first and the second plastic material do not enter into a cohesive connection;
  wherein after step d), in a further process step d2), a sealing element (200) is mounted on the fourth tool portion (9), said fourth tool portion (9) having a holding element (9b) projecting into the mould cavity (10) of the fourth tool portion (9) that is designed to hold the sealing element (200).

18. The method according to claim 17, characterised in that the sealing element (200) in process step e) is pressed against the hollow cylindrical end piece (106) of the syringe body (102).

19. The method according to claim 17, characterised in that the sealing element (200) after process step f) is surrounded by the second plastic material, while the sealing element (200) after the demoulding of the fourth tool portion (9) is still pressed against the hollow cylindrical end piece (106) of the syringe body (102).

* * * * *